United States Patent
Allerdings et al.

(10) Patent No.: US 10,195,351 B2
(45) Date of Patent: Feb. 5, 2019

(54) SUPPLEMENTAL DEVICE FOR ATTACHMENT TO AN INJECTION DEVICE

(71) Applicant: SANOFI-AVENTIS DEUTSCHLAND GMBH, Frankfurt am Main (DE)

(72) Inventors: Alexander Allerdings, Frankfurt am Main (DE); Stephan Mueller-Pathle, Frankfurt am Main (DE); André Baran, Steinfurt (DE); Kay Behrendt, Bad Bentheim (DE)

(73) Assignee: Sanofi-Aventis Deutschland GMBH, Frankfurt am Main (DE)

( * ) Notice: Subject to any disclaimer, the term of this patent is extended or adjusted under 35 U.S.C. 154(b) by 0 days.

(21) Appl. No.: 14/373,138

(22) PCT Filed: Feb. 8, 2013

(86) PCT No.: PCT/EP2013/052509
§ 371 (c)(1),
(2) Date: Jul. 18, 2014

(87) PCT Pub. No.: WO2013/120777
PCT Pub. Date: Aug. 22, 2013

(65) Prior Publication Data
US 2015/0032059 A1 Jan. 29, 2015

Related U.S. Application Data

(60) Provisional application No. 61/605,448, filed on Mar. 1, 2012.

(30) Foreign Application Priority Data

Feb. 13, 2012 (EP) .................................... 12155202

(51) Int. Cl.
*A61M 5/315* (2006.01)
*A61M 5/24* (2006.01)
(Continued)

(52) U.S. Cl.
CPC .......... *A61M 5/31525* (2013.01); *A61M 5/24* (2013.01); *G06F 19/00* (2013.01);
(Continued)

(58) Field of Classification Search
CPC .. A61M 2005/3125; A61M 2005/3126; A61M 5/002; A61M 5/31533;
(Continued)

(56) References Cited

U.S. PATENT DOCUMENTS 533,575 A 2/1895 Wilkens
5,226,895 A 7/1993 Harris
(Continued)

FOREIGN PATENT DOCUMENTS

EP 0937471 8/1999
EP 0937476 8/1999
(Continued)

OTHER PUBLICATIONS

International Search Report for Int. App. No. PCT/EP2013/052509, completed Apr. 19, 2013.
(Continued)

*Primary Examiner* — Theodore Stigell
*Assistant Examiner* — James D Ponton
(74) *Attorney, Agent, or Firm* — Fish & Richardson P.C.

(57) ABSTRACT

A supplemental device for attachment to an injection device is presented having a display; a processor arrangement; a dose dialed detector operable to detect a dose of medicament dialed into an attached injection device; a dose delivery determiner for determining that a dose of medicament has been delivered; a quantity determiner determining a quantity of medicament that has been delivered; and a clock configured to determine a current time. The processor arrangement is configured when the supplemental device is in a default mode to display both a quantity of medicament that was
(Continued)

delivered since a last dose and a time elapsed since delivery of the last dose.

16 Claims, 12 Drawing Sheets

(51) Int. Cl.
*G06F 19/00* (2018.01)
*G16H 40/63* (2018.01)
*A61M 5/00* (2006.01)
*A61M 5/31* (2006.01)

(52) U.S. Cl.
CPC ......... *G06F 19/3468* (2013.01); *G16H 40/63* (2018.01); *A61M 5/002* (2013.01); *A61M 2005/3125* (2013.01); *A61M 2005/3126* (2013.01); *A61M 2205/3306* (2013.01); *A61M 2205/50* (2013.01); *A61M 2205/502* (2013.01); *A61M 2205/505* (2013.01); *A61M 2205/52* (2013.01); *A61M 2205/581* (2013.01); *A61M 2205/582* (2013.01); *A61M 2205/8206* (2013.01); *A61M 2209/04* (2013.01)

(58) Field of Classification Search
CPC ...... A61M 5/31525; A61M 2205/3306; A61M 2205/502; A61M 2205/505; A61M 2205/50; A61M 2205/52; A61M 2209/04; A61M 2205/6081; A61M 2205/6072; A61M 2205/6063; A61M 5/31568; G06F 19/3406; G06F 19/3468
See application file for complete search history.

(56) References Cited

U.S. PATENT DOCUMENTS

| | | | |
|---|---|---|---|
| 5,279,586 A | 1/1994 | Balkwill | |
| 5,304,152 A | 4/1994 | Sams | |
| 5,320,609 A | 6/1994 | Haber et al. | |
| 5,383,865 A | 1/1995 | Michel | |
| 5,480,387 A | 1/1996 | Gabriel et al. | |
| 5,505,704 A | 4/1996 | Pawelka et al. | |
| 5,582,598 A | 12/1996 | Chanoch | |
| 5,626,566 A | 5/1997 | Petersen et al. | |
| 5,674,204 A | 10/1997 | Chanoch | |
| 5,688,251 A | 11/1997 | Chanoch | |
| 5,724,021 A * | 3/1998 | Perrone | G04B 47/00 221/15 |
| 5,921,966 A | 7/1999 | Bendek et al. | |
| 5,961,495 A | 10/1999 | Walters et al. | |
| 6,004,297 A | 12/1999 | Steenfeldt-Jensen et al. | |
| 6,193,698 B1 | 2/2001 | Kirchhofer et al. | |
| 6,221,046 B1 | 4/2001 | Burroughs et al. | |
| 6,235,004 B1 | 5/2001 | Steenfeldt-Jensen et al. | |
| 6,248,095 B1 | 6/2001 | Giambattista et al. | |
| 6,899,698 B2 | 5/2005 | Sams | |
| 6,936,032 B1 | 8/2005 | Bush, Jr. et al. | |
| 7,241,278 B2 | 7/2007 | Moller | |
| 2002/0032429 A1* | 3/2002 | Hjertman | A61M 5/145 604/500 |
| 2002/0045854 A1* | 4/2002 | Royo | A61M 25/1018 604/97.03 |
| 2002/0052578 A1 | 5/2002 | Moller | |
| 2002/0120235 A1 | 8/2002 | Enggaard | |
| 2003/0050609 A1 | 3/2003 | Sams | |
| 2004/0059299 A1 | 3/2004 | Moller | |
| 2004/0210199 A1 | 10/2004 | Atterbury et al. | |
| 2004/0267207 A1 | 12/2004 | Veasey et al. | |
| 2005/0090781 A1 | 4/2005 | Baba et al. | |
| 2005/0113765 A1 | 5/2005 | Veasey et al. | |
| 2006/0153693 A1 | 7/2006 | Fiechter et al. | |
| 2008/0188813 A1* | 8/2008 | Miller | A61M 5/14566 604/189 |
| 2009/0275916 A1 | 11/2009 | Harms et al. | |
| 2010/0286612 A1* | 11/2010 | Cirillo | A61M 5/31525 604/111 |
| 2013/0079708 A1 | 3/2013 | Wimpenny et al. | |
| 2014/0194825 A1* | 7/2014 | Nielsen | A61M 5/24 604/189 |

FOREIGN PATENT DOCUMENTS

| | | |
|---|---|---|
| JP | H11-500643 | 1/1999 |
| JP | 2004-523282 A | 8/2004 |
| JP | 2007-252481 | 10/2007 |
| JP | 2008-516711 | 5/2008 |
| JP | 2011-521744 A | 7/2011 |
| TW | 201200190 A | 1/2012 |
| WO | 97/30742 | 8/1997 |
| WO | 99/38554 | 8/1999 |
| WO | 01/10484 | 2/2001 |
| WO | 02/058767 A1 | 8/2002 |
| WO | 03/057286 A1 | 7/2003 |
| WO | 2006/045525 A1 | 5/2006 |
| WO | 2009/024562 | 2/2009 |
| WO | 2010/128493 | 11/2010 |
| WO | 2011/067187 A1 | 6/2011 |
| WO | 2011/089205 A2 | 7/2011 |
| WO | 2011/117212 | 9/2011 |

OTHER PUBLICATIONS

International Preliminary Report on Patentability in International Application No. PCT/EP2013/052509, dated Aug. 19, 2014, 6 pages.

* cited by examiner

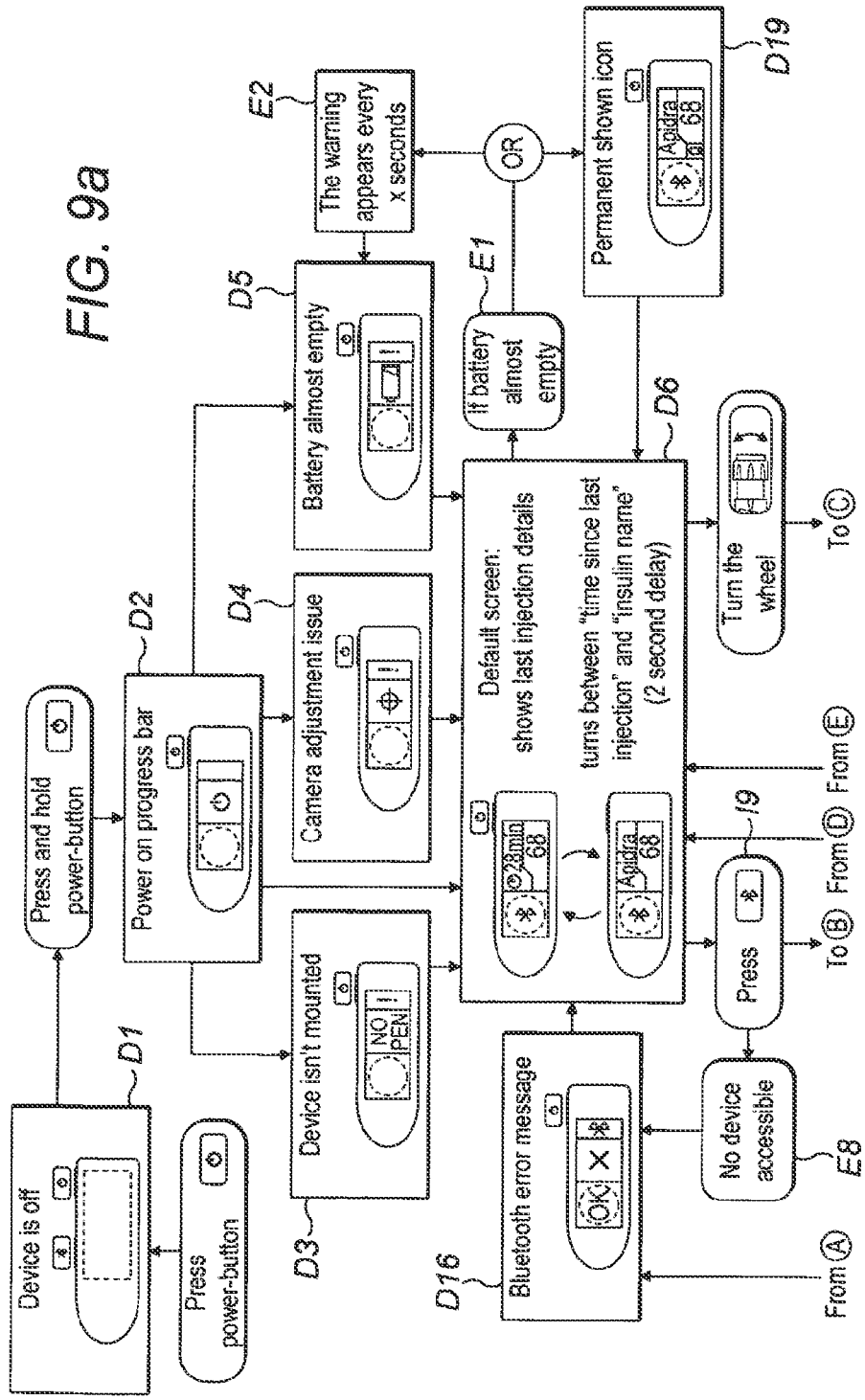

SUPPLEMENTAL DEVICE FOR ATTACHMENT TO AN INJECTION DEVICE

CROSS REFERENCE TO RELATED APPLICATIONS

The present application is a U.S. National Phase Application pursuant to 35 U.S.C. § 371 of International Application No. PCT/EP2013/052509 filed Feb. 8, 2013, which claims priority to European Patent Application No. 12155202.0 filed Feb. 13, 2012, and U.S. Provisional Patent Application No. 61/605,448, filed Mar. 1, 2012. The entire disclosure contents of these applications are herewith incorporated by reference into the present application.

TECHNICAL FIELD

The present invention relates to a supplemental device for attachment to an injection device.

BACKGROUND

A variety of diseases exists that require regular treatment by injection of a medicament. Such injection can be performed by using injection devices, which are applied either by medical personnel or by patients themselves. As an example, type-1 and type-2 diabetes can be treated by patients themselves by injection of insulin doses, for example once or several times per day. For instance, a pre-filled disposable insulin pen can be used as an injection device. Alternatively, a re-usable pen may be used. A re-usable pen allows replacement of an empty medicament cartridge by a new one. Either pen may come with a set of one-way needles that are replaced before each use. The insulin dose to be injected can then for instance be manually selected at the insulin pen by turning a dosage knob and observing the actual dose from a dose window or display of the insulin pen. The dose is then injected by inserting the needle into a suited skin portion and pressing an injection button of the insulin pen. To be able to monitor insulin injection, for instance to prevent false handling of the insulin pen or to keep track of the doses already applied, it is desirable to measure information related to a condition and/or use of the injection device, such as for instance information on the injected insulin type and dose. In this respect, WO 2009/024562 discloses a medical device with a value sensor. A Radio Frequency Identification (RFID) unit comprises a value sensor such as a pressure sensor and is integrated with a liquid medicament container to enable wireless pressure or other medicament relevant parameter value monitoring. The liquid medicament container is coupled with a first housing part of the medical device, which first housing part may for instance constitute a pre-filled disposable injection device. The RFID unit communicates wirelessly with a control circuit that is contained in a second housing part of the medical device that is releasably attached to the first housing part. The control circuit is adapted to process the values measured by the RFID unit, to compare it with pre-defined values and to provide an alert to the user if the measured values fall outside normal operating conditions, and to communicate data relating to the measured values to an external device for further data processing.

The control circuit of the medical device described in WO 2009/024562 can thus be used with a series of pre-filled disposable injection devices, but the requirement that the RFID unit with the value sensor is contained in the medicament container of the pre-filled disposable injection devices significantly increases the costs of the pre-filled disposable injection device.

It has been described, for instance in WO 2011/117212 to provide a supplementary device comprising a mating unit for releasably attaching the device to an injection device The device includes a camera and is configured to perform optical character recognition (OCR) on captured images visible through a dosage window of the injection pen, thereby to determine a dose of medicament that has been dialed into the injection device.

SUMMARY

According to a first aspect of the present invention, there is provided a supplemental device for attachment to an injection device, the supplemental device comprising:
 a display;
 a processor arrangement;
 a dose dialed detector operable to detect a dose of medicament dialed into an attached injection device;
 a dose delivery determiner for determining that a dose of medicament has been delivered;
 a quantity determiner for determining a quantity of medicament that has been delivered; and
 a clock configured to determine a current time;
 the processor arrangement being configured when the supplemental device is in a default mode to display both a quantity of medicament that was delivered since a last dose and a time elapsed since delivery of the last dose.

The processor arrangement may be configured when the supplemental device is in the default mode to display continually a quantity of medicament that was delivered since a last dose and to display intermittently a time elapsed since delivery of the last dose.

The processor arrangement may be configured when the supplemental device is in the default mode to display a quantity of medicament that was delivered since a last dose, a time elapsed since delivery of the last dose, and an identify of the medicament delivered in the last dose.

The processor arrangement may be configured when the supplemental device is in the default mode to display continually a quantity of medicament that was delivered since a last dose, and to alternate between displaying a time elapsed since delivery of the last dose and an identify of the medicament delivered in the last dose.

The processor arrangement may be configured when the supplemental device is in the default mode to respond to detection of a dose being dialed to enter a dose dialling mode and to cause display of a dose currently dialed into the attached injection device.

The processor arrangement may be configured when the supplemental device is in the dose dialling mode to respond to detection of dose dialling having stopped to enter a dose dialed mode and to cause display of a dose currently dialed into the attached injection device and to display a graphic or text indicating that dose delivery is possible. Here, the processor arrangement may be configured when the supplemental device is in the dose dialed mode to respond to detection of a confirm/OK input by a user to cause display of a remaining dose dialed into the attached injection device.

The processor arrangement may be configured to respond to detection of a dose having been delivered to enter a dose delivered mode. Here, the processor arrangement may be configured to detect that a dose has been delivered by detecting that a dose has been fully delivered or by detecting that dose delivery has ceased and been confirmed by a user. Alternatively or additionally the processor arrangement may be configured when the supplemental device is in the dose delivered mode to cause display of a delivered dose. The processor arrangement may be configured to respond to the supplemental device being detected to be in the dose delivered mode to record a time of dose delivery.

The supplemental device may comprise at least two hardware keys, including a power on/off key and a confirm/OK key, wherein the wherein the processor arrangement is configured to respond to detection of operation of the confirm/OK key by transitioning between different modes of operation.

The display may be a touch-sensitive display and the processor arrangement may be configured to cause display of a virtual button on the touch-sensitive display, the display indicating an action that the processor arrangement is configured to implement in response to receiving a user input at the virtual button.

A second aspect of the invention provides a system comprising a supplemental device as claimed in any preceding claim and an injection device.

A third aspect of the invention provides a method of operating a supplemental device attached to an injection device, the supplemental device being as described above, the method comprising:
  detecting a dose of medicament dialed into the injection device;
  determining that a dose of medicament has been delivered;
  determining a quantity of medicament that has been delivered; and
  when the supplemental device is in a default mode, displaying both a quantity of medicament that was delivered since a last dose and a time elapsed since delivery of the last dose.

A fourth aspect of the invention provides a computer program comprising machine readable instructions that when executed by a processor arrangement of a supplemental device attachable to an injection device, the supplemental device being as described above, cause the supplemental device to perform a method comprising:
  detecting a dose of medicament dialed into the injection device;
  determining that a dose of medicament has been delivered;
  determining a quantity of medicament that has been delivered; and
  when the supplemental device is in a default mode, displaying both a quantity of medicament that was delivered since a last dose and a time elapsed since delivery of the last dose.

Embodiments of the invention will now be described, by way of example only, with reference to the accompanying drawings.

BRIEF DESCRIPTION OF THE FIGURES

The figures show:
FIG. 1b shows a perspective view of some detail of the injection device of FIG. 1a;
FIG. 4: a schematic view of the supplementary device of FIG. 2a in a state where it is attached to the injection device of FIG. 1a.

DETAILED DESCRIPTION

In the following, embodiments of the present invention will be described with reference to an insulin injection device. The present invention is however not limited to such application and may equally well be deployed with injection devices that eject other medicaments, or with other types of medical devices.

Figure 1A:
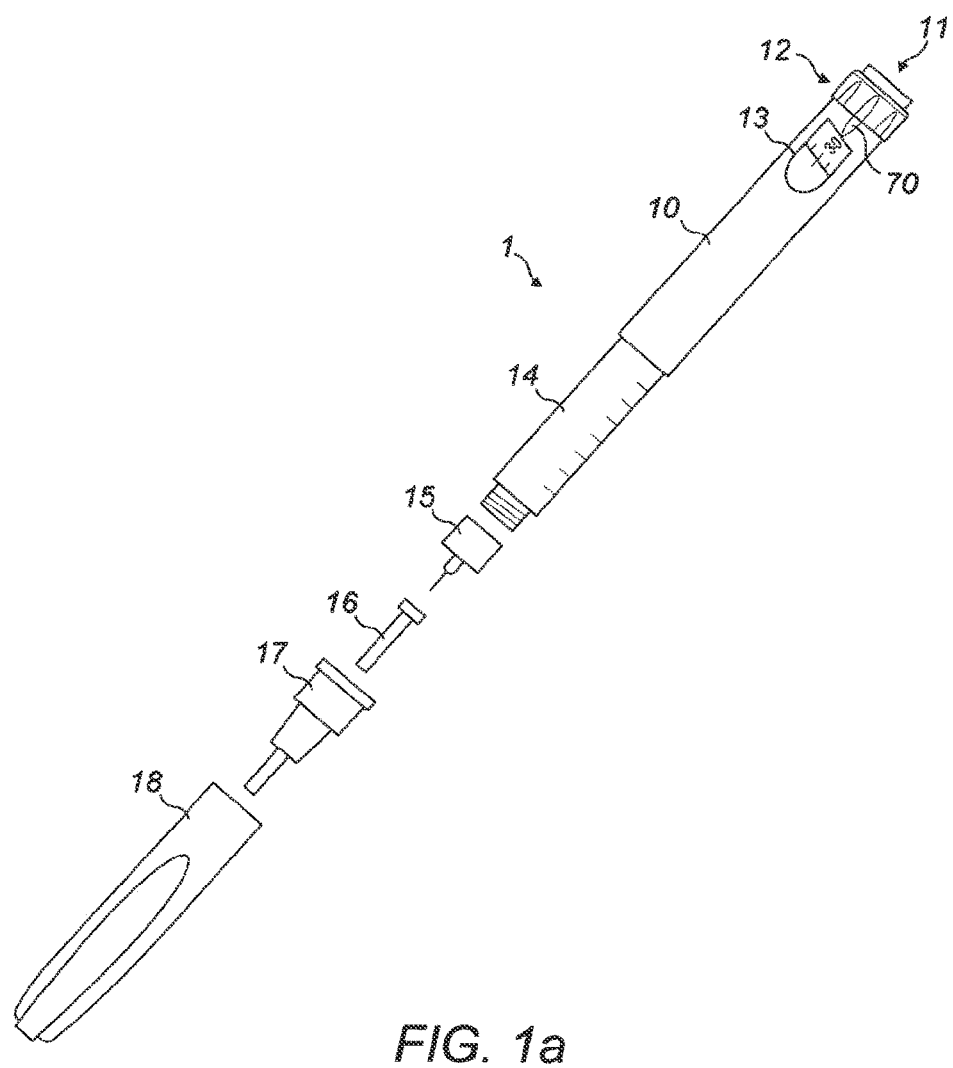
FIG. 1a: an exploded view of an injection device.
Figure 1B:
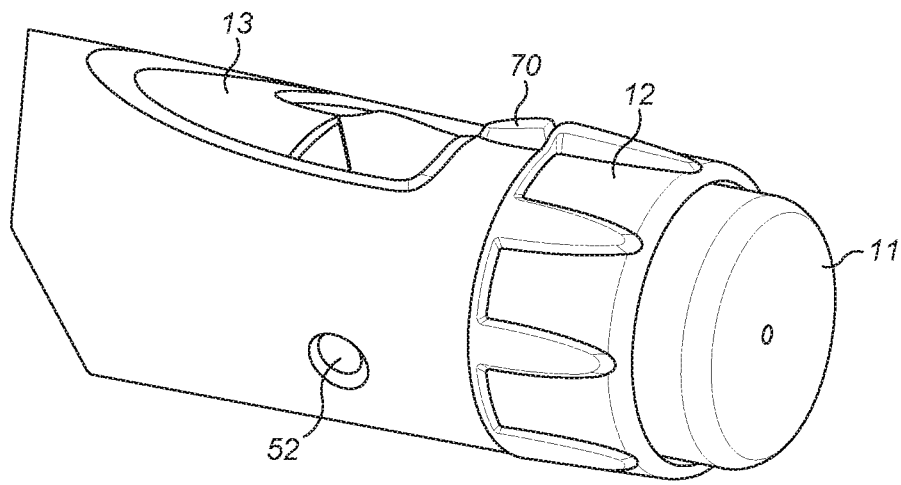

FIG. 1a is an exploded view of an injection device 1, which may for instance represent Sanofi's Solostar (R) insulin injection pen.

The injection device 1 of FIG. 1a is a pre-filled, disposable injection pen that comprises a housing 10 and contains an insulin container 14, to which a needle 15 can be affixed. The needle is protected by an inner needle cap 16 and an outer needle cap 17, which in turn can be covered by a cap 18. An insulin dose to be ejected from injection device 1 can be selected by turning the dosage knob 12, and the selected dose is then displayed via dosage window 13, for instance in multiples of so-called International Units (IU), wherein one IU is the biological equivalent of about 45.5 micrograms of pure crystalline insulin (1/22 mg). An example of a selected dose displayed in dosage window 13 may for instance be 30 IUs, as shown in FIG. 1a. It should be noted that the selected dose may equally well be displayed differently, for instance by means of an electronic display.

Turning the dosage knob 12 causes a mechanical click sound to provide acoustical feedback to a user. The numbers displayed in dosage window 13 are printed on a sleeve that is contained in housing 10 and mechanically interacts with a piston in insulin container 14. When needle 15 is stuck into a skin portion of a patient, and then injection button 11 is pushed, the insulin dose displayed in display window 13 will be ejected from injection device 1. When the needle 15 of injection device 1 remains for a certain time in the skin portion after the injection button 11 is pushed, a high percentage of the dose is actually injected into the patient's body. Ejection of the insulin dose also causes a mechanical click sound, which is however different from the sounds produced when using dosage knob 12.

Injection device 1 may be used for several injection processes until either insulin container 14 is empty or the expiration date of injection device 1 (e.g. 28 days after the first use) is reached.

Furthermore, before using injection device 1 for the first time, it may be necessary to perform a so-called "prime shot" to remove air from insulin container 14 and needle 15, for instance by selecting two units of insulin and pressing injection button 11 while holding injection device 1 with the needle 15 upwards.

For simplicity of presentation, in the following, it will be exemplarily assumed that the ejected doses substantially correspond to the injected doses, so that, for instance when making a proposal for a dose to be injected next, this dose equals the dose that has to ejected by the injection device. Nevertheless, differences (e.g. losses) between the ejected doses and the injected doses may of course be taken into account.

Figure 2A:
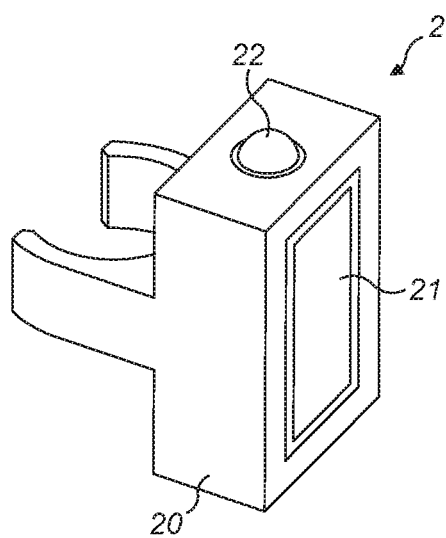
FIG. 2a: a schematic illustration of a supplementary device to be releasably attached to the injection device of FIG. 1a according to an embodiment of the present invention.

FIG. 2a is a schematic illustration of an embodiment of a supplementary device 2 to be releasably attached to injection device 1 of FIG. 1a. Supplementary device 2 comprises a housing 20 with a mating unit configured and embrace the housing 10 of injection device 1 of FIG. 1a, so that supplementary device 2 sits tightly on housing 10 of injection device 1, but is nevertheless removable from injection device 1, for instance when injection device 1 is empty and has to be replaced. FIG. 2a is highly schematic, and details of the physical arrangement are described below with reference to FIG. 2b.

Supplementary device 2 contains optical and acoustical sensors for gathering information from injection device 1. Information is displayed via display unit 21 of supplementary device 2. The dosage window 13 of injection device 1 is obstructed by supplementary device 2 when attached to injection device 1.

Supplementary device 2 further comprises three user input transducers, illustrated schematically as a button 22. These input transducers 22 allow a user to turn on/off supplementary device 2, to trigger actions (for instance to cause establishment of a connection to or a pairing with another device, and/or to trigger transmission of information from supplementary device 2 to another device), or to confirm something.

Figure 2B:
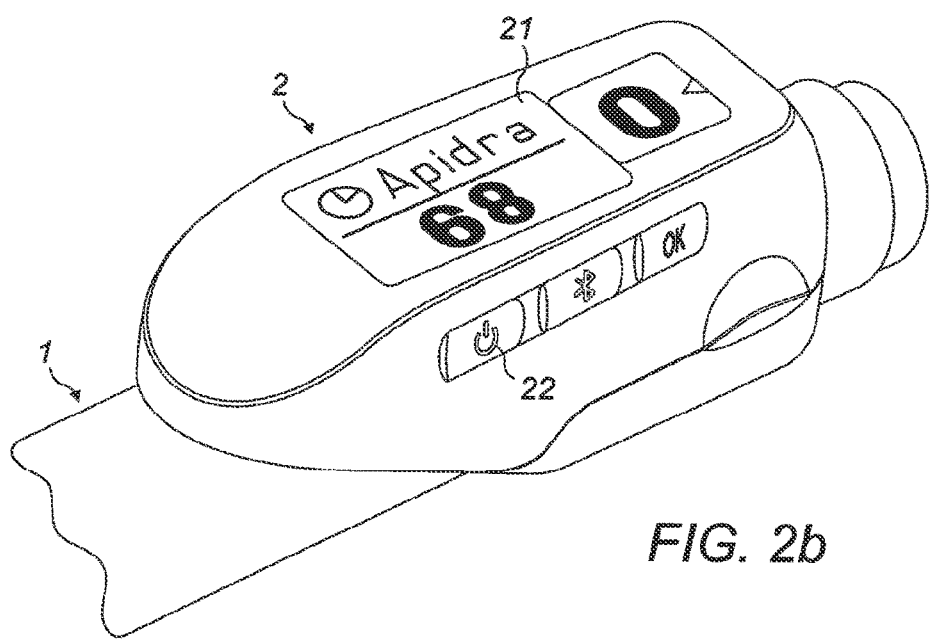
FIG. 2b: a perspective view of a supplementary device to be releasably attached to the injection device of FIG. 1a according to various embodiments of the present invention.

FIG. 2b is a schematic illustration of a second embodiment of a supplementary device 2 to be releasably attached to injection device 1 of FIG. 1a. Supplementary device 2 comprises a housing 20 with a mating unit configured and embrace the housing 10 of injection device 1 of FIG. 1a, so that supplementary device 2 sits tightly on housing 10 of injection device 1, but is nevertheless removable from injection device 1.

Information is displayed via display unit 21 of supplementary device 2. The dosage window 13 of injection device 1 is obstructed by supplementary device 2 when attached to injection device 1.

Supplementary device 2 further comprises three user input buttons or switches. A first button 22 is a power on/off button, via which the supplementary device 2 may for instance be turned on and off. A second button 33 is a communications button. A third button 34 is a confirm or OK button. The buttons 22, 33, 34 may be any suitable form of mechanical switch. These input buttons 22 allow a user to turn on/off supplementary device 2, to trigger actions (for instance to cause establishment of a connection to or a pairing with another device, and/or to trigger transmission of information from supplementary device 2 to another device), or to confirm something.

Figure 2C:
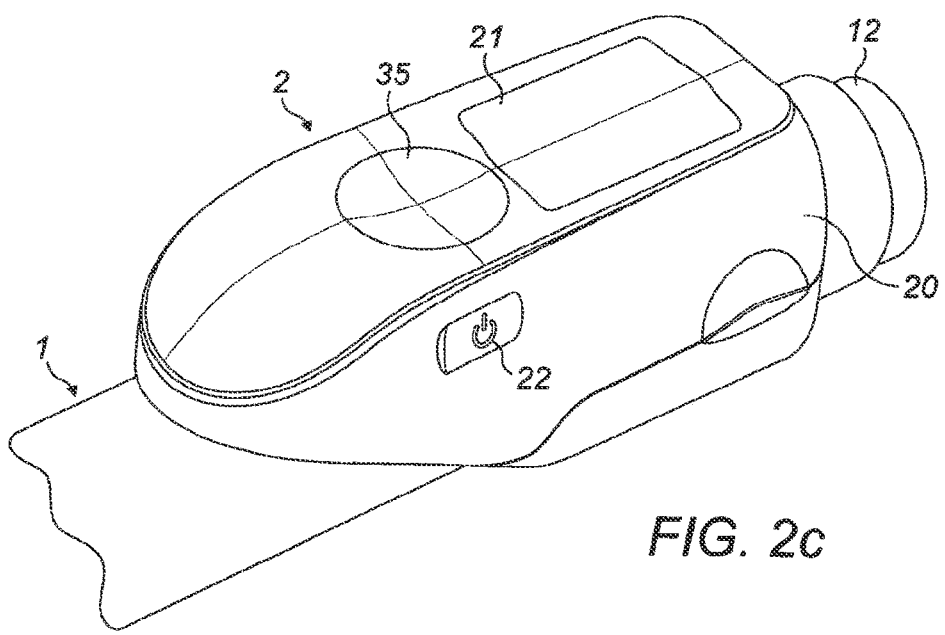
FIG. 2c: a perspective view of a supplementary device to be releasably attached to the injection device of FIG. 1a according to other embodiments of the present invention.

FIG. 2c is a schematic illustration of a third embodiment of a supplementary device 2 to be releasably attached to injection device 1 of FIG. 1a. Supplementary device 2 comprises a housing 20 with a mating unit configured and embrace the housing 10 of injection device 1 of FIG. 1a, so that supplementary device 2 sits tightly on housing 10 of injection device 1, but is nevertheless removable from injection device 1.

Information is displayed via display unit 21 of the supplementary device 2. The dosage window 13 of injection device 1 is obstructed by supplementary device 2 when attached to injection device 1.

Supplementary device 2 further comprises a touch-sensitive input transducer 35. It also comprises a single user input button or switch 22. The button 22 is a power on/off button, via which the supplementary device 2 may for instance be turned on and off. The touch sensitive input transducer 35 can be used to trigger actions (for instance to cause establishment of a connection to or a pairing with another device, and/or to trigger transmission of information from supplementary device 2 to another device), or to confirm something.

Figure 3A:
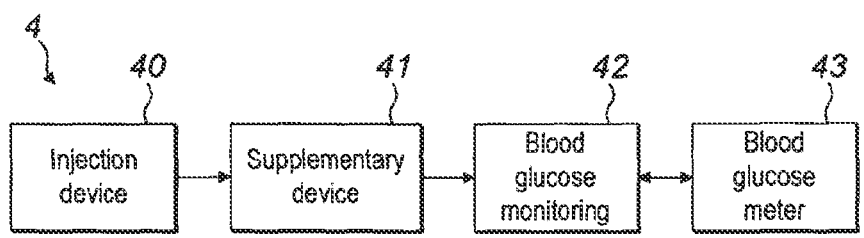
FIGS. 3a and 3b: possible distributions of functions among devices when using a supplementary device (such as the supplementary devices of FIGS. 2a, 2b and 2c) together with an injection device.
Figure 3B:
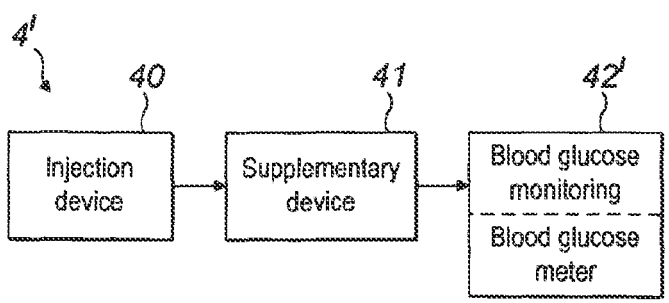

FIGS. 3A and 3b show possible distributions of functions among devices when using a supplementary device (such as the supplementary devices of FIGS. 2a and 2b) together with an injection device.

In constellation 4 of FIG. 3a, the supplementary device 41 (such as the supplementary devices of FIGS. 2a and 2b) determines information from injection device 40, and provides this information (e.g. type and/or dose of the medicament to be injected) to a blood glucose monitoring system 42 (e.g. via a wired or wireless connection).

Blood glucose monitoring system 42 (which may for instance be embodied as desktop computer, personal digital assistant, mobile phone, tablet computer, notebook, netbook or ultrabook) keeps a record of the injections a patient has received so far (based on the ejected doses, for instance by assuming that the ejected doses and the injected doses are the same, or by determining the injected doses based on the ejected doses, for instance be assuming that a pre-defined percentage of the ejected dose is not completely received by the patient). Blood glucose monitoring system 42 may for instance propose a type and/or dose of insulin for the next injection for this patient. This proposal may be based on information on one or more past injections received by the patient, and on a current blood glucose level, that is measured by blood glucose meter 43 and provided (e.g. via a wired or wireless connection) to blood glucose monitoring system 42. Therein, blood glucose meter 43 may be embodied as a separate device that is configured to receive a small blood probe (for instance on a carrier material) of a patient and to determine the blood glucose level of the patient based on this blood probe. Blood glucose meter 43 may however also be a device that is at least temporarily implanted into the patient, for instance in the patient's eye or beneath the skin.

FIG. 3b is a modified constellation 4' where the blood glucose meter 43 of FIG. 3a has been included into blood glucose monitoring system 42 of FIG. 3a, thus yielding the modified blood glucose monitoring system 42' of FIG. 3b. The functionalities of injection device 40 and supplementary device 41 of FIG. 3a are not affected by this modification. Also the functionality of blood glucose monitoring system 42 and blood glucose meter 43 combined into blood glucose monitoring system 42' are basically unchanged, apart from the fact that both are now comprised in the same device, so that external wired or wireless communication between these devices is no longer necessary. However, communication between blood glucose monitoring system 42 and blood glucose meter 43 takes place within system 42'.

Figure 4:
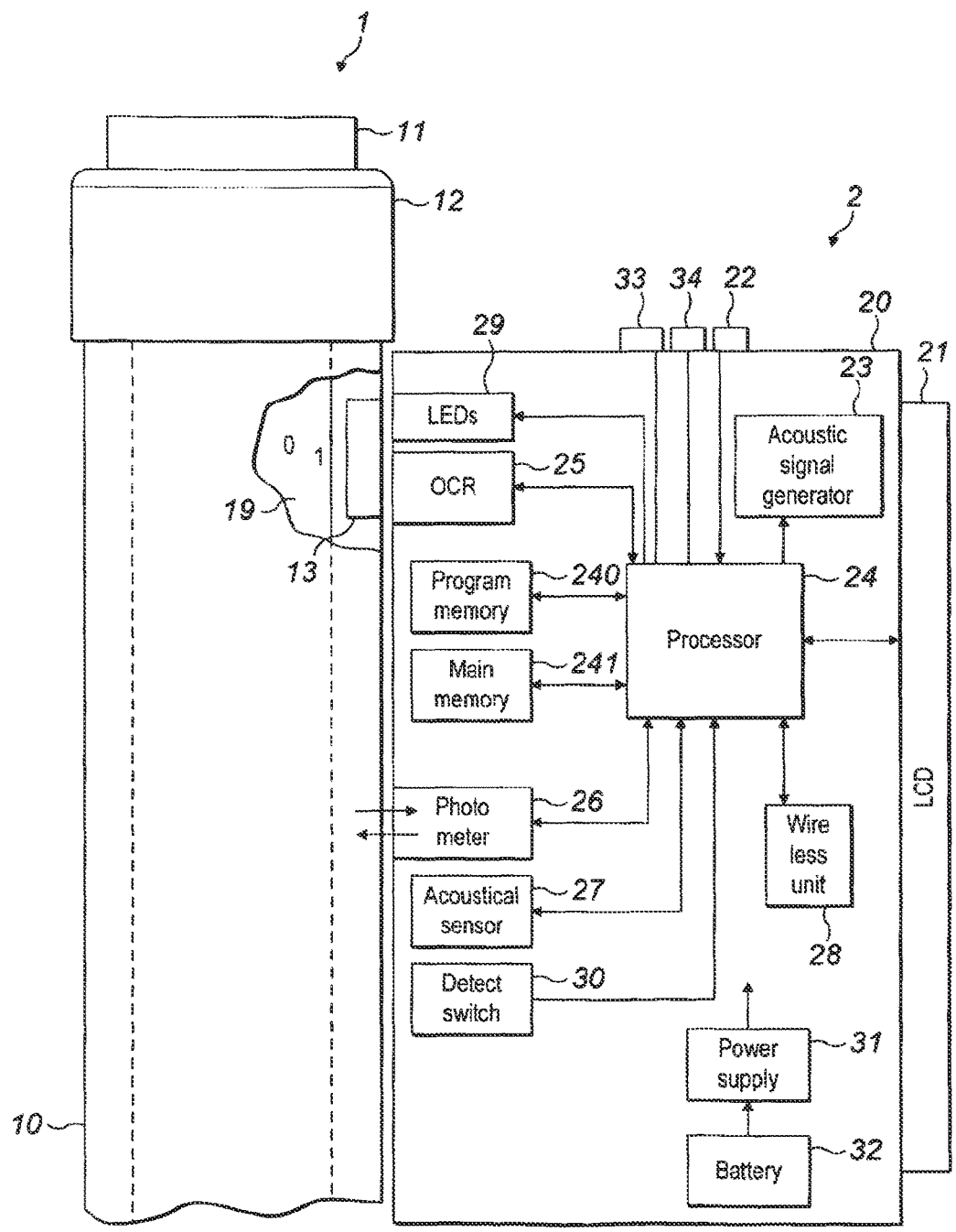

FIG. 4 shows a schematic view of the supplementary device 2 of FIG. 2a in a state where it is attached to injection device 1 of FIG. 1a.

With the housing 20 of supplementary device 2, a plurality of components are comprised. These are controlled by a processor 24, which may for instance be a microprocessor, a Digital Signal Processor (DSP), Application Specific Integrated Circuit (ASIC), Field Programmable Gate Array (FPGA) or the like. Processor 24 executes program code (e.g. software or firmware) stored in a program memory 240, and uses a main memory 241, for instance to store intermediate results. Main memory 241 may also be used to store a logbook on performed ejections/injections. Program memory 240 may for instance be a Read-Only Memory (ROM), and main memory may for instance be a Random Access Memory (RAM).

In embodiments such as those shown in FIG. 2b, processor 24 interacts with a first button 22, via which supplementary device 2 may for instance be turned on and off. A second button 33 is a communications button. The second button may be used to trigger establishment of a connection to another device, or to trigger a transmission of information to another device. A third button 34 is a confirm or OK button. The third button 34 can be used to acknowledge information presented to a user of supplementary device 2.

In embodiments such as those shown in FIG. 2c, two of the buttons 33, 34 may be omitted. Instead, one or more capacitive sensors or other touch sensors are provided.

Processor 24 controls a display unit 21, which is presently embodied as a Liquid Crystal Display (LCD). Display unit 21 is used to display information to a user of supplementary device 2, for instance on present settings of injection device 1, or on a next injection to be given. Display unit 21 may also be embodied as a touch-screen display, for instance to receive user input.

Processor 24 also controls an optical sensor 25, embodied as an Optical Character Recognition (OCR) reader, that is capable of capturing images of the dosage window 13, in which a currently selected dose is displayed (by means of numbers printed on the sleeve 19 contained in injection device 1, which numbers are visible through the dosage window 13). OCR reader 25 is further capable of recognizing characters (e.g. numbers) from the captured image and to provide this information to processor 24. Alternatively, unit 25 in supplementary device 2 may only be an optical sensor, e.g. a camera, for capturing images and providing information on the captured images to processor 24. Then processor 24 is responsible for performing OCR on the captured images.

Processor 24 also controls light-sources such as light emitting diodes (LEDs) 29 to illuminate the dosage window 13, in which a currently selected dose is displayed. A diffuser may be used in front of the light-sources, for instance a diffuser made from a piece of acrylic glass. Furthermore, the optical sensor may comprise a lens (e.g. an aspheric lens) leading to a magnification (e.g. a magnification of more than 3:1).

Processor 24 further controls a photometer 26, that is configured to determine an optical property of the housing 10 of injection device 1, for example a colour or a shading. The optical property may only be present in a specific portion of housing 10, for example a colour or colour coding of sleeve 19 or of an insulin container comprised within injection device 1, which colour or colour coding may for instance be visible through a further window in housing 10 (and/or in sleeve 19). Information on this colour is then provided to processor 24, which may then determine the type of injection device 1 or the type of insulin contained in injection device 1 (e.g. SoloStar Lantus with purple colour and SoloStar Apidra with blue colour). Alternatively, a camera unit may be used instead of photometer 26, and an image of the housing, sleeve or insulin container may then be provided to processor 24 to determine the colour of the housing, sleeve or insulin container by means of image processing. Further, one or more light sources may be provided to improve reading of photometer 26. The light source may provide light of a certain wavelength or spectrum to improve colour detection by photometer 26. The light source may be arranged in such a way that unwanted reflections, for example by dosage window 13, are avoided or reduced. In an example embodiment, instead of or in addition to photometer 26, a camera unit may be deployed to detect a code (for instance a bar code, which may for instance be a one- or two-dimensional bar code) related to the injection device and/or the medicament contained therein. This code may for instance be located on the housing 10 or on a medicament container contained in injection device 1, to name but a few examples. This code may for instance indicate a type of the injection device and/or the medicament, and/or further properties (for instance a expiration date).

Processor 24 further controls (and/or receives signals from) an acoustic sensor 27, which is configured to sense sounds produced by injection device 1. Such sounds may for instance occur when a dose is dialed by turning dosage knob 12 and/or when a dose is ejected/injected by pressing injection button 11, and/or when a prime shot is performed. These actions are mechanically similar but nevertheless sound differently (this may also be the case for electronic sounds that indicate these actions). Either the acoustic sensor 27 and/or processor 24 may be configured to differentiate these different sounds, for instance to be able to safely recognize that an injection has taken place (rather than a prime shot only).

Processor 24 further controls an acoustical signal generator 23, which is configured to produce acoustical signals that may for instance be related to the operating status of injection device 1, for instance as feedback to the user. For example, an acoustical signal may be launched by acoustical signal generator 23 as a reminder for the next dose to be injected or as a warning signal, for instance in case of misuse. Acoustical signal generator may for instance be embodied as a buzzer or loudspeaker. In addition to or as an alternative to acoustical signal generator 23, also a haptic signal generator (not shown) may be used to provide haptic feedback, for instance by means of vibration.

Processor 24 controls a wireless unit 28, which is configured to transmit and/or receive information to/from another device in a wireless fashion. Such transmission may for instance be based on radio transmission or optical transmission. In some embodiments, the wireless unit 28 is a Bluetooth transceiver. Alternatively, wireless unit 28 may be substituted or complemented by a wired unit configured to transmit and/or receive information to/from another device in a wire-bound fashion, for instance via a cable or fibre connection. When data is transmitted, the units of the data (values) transferred may be explicitly or implicitly defined. For instance, in case of an insulin dose, always International Units (IU) may be used, or otherwise, the used unit may be transferred explicitly, for instance in coded form.

Processor 24 receives an input from a pen detection switch 30, which is operable to detect whether the pen 1 is present, i.e. to detect whether the supplementary device 2 is coupled to the injection device 1.

A battery 32 powers the processor 24 and other components by way of a power supply 31.

The supplementary device 2 of FIG. 4 is thus capable of determining information related to a condition and/or use of injection device 1. This information is displayed on the display 21 for use by the user of the device. The information may be either processed by supplementary device 2 itself, or may at least partially be provided to another device (e.g. a blood glucose monitoring system).

The processor 24 constitutes a processor arrangement. The OCR reader 25 constitutes a dose dialed detector operable to detect a dose of medicament dialed. The OCR reader 25 also constitutes a dose delivery determiner for determining that a dose of medicament has been delivered. The OCR reader 25 and the processor 24 together constitute a quantity determiner for determining a quantity of medicament that has been delivered. The processor 24 provides a function of a clock configured to determine a current time.

Figure 5A:
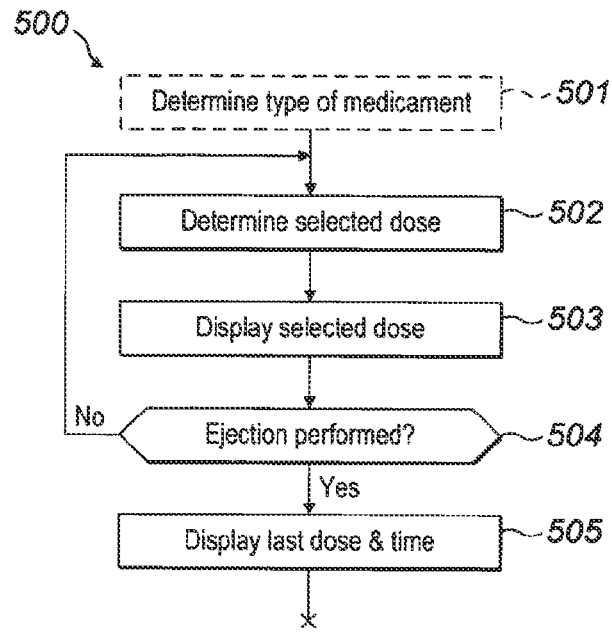
FIG. 5a: a flowchart of a method used in various embodiments.
Figure 5B:
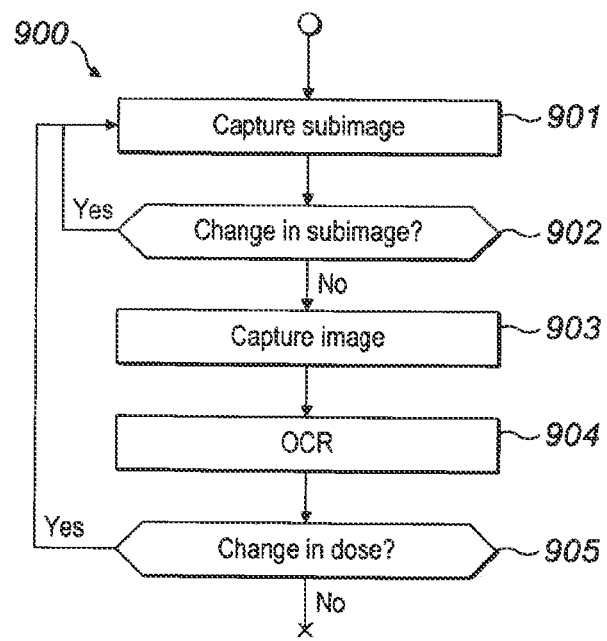
FIG. 5b: a flowchart of a further method used in various embodiments.
Figure 5C:
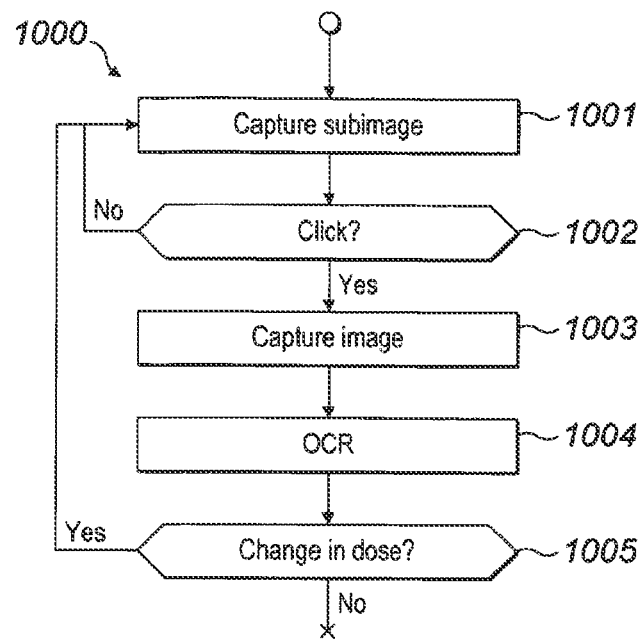
FIG. 5c: a flowchart of a still further method used in various embodiments.

FIGS. 5a-5c are flowcharts of embodiments of methods according to the present invention. These methods may for instance be performed by processor 24 of supplementary device 2 (see FIGS. 2b and 4), but also by a processor of supplementary device 3 of FIG. 2b, and may for instance be stored in program memory 240 of supplementary device 2, which may for instance take the shape of tangible storage medium 60 of FIG. 6.

FIG. 5a shows method steps that are performed in scenarios as shown in FIGS. 3a and 3b, where information read by supplementary device 41 from injection device 40 is provided to blood glucose monitoring system 42 or 42' without receiving information back from blood glucose monitoring system 42 or 42'.

The flowchart 500 starts for instance when the supplementary device is turned on or is otherwise activated. In a step 501, a type of medicament, for example insulin, provided by the injection device is determined, for instance based on colour recognition or based on recognition of a code printed on injection device or a component thereof as already described above. Detection of the type of medicament may not be necessary if a patient always takes the same type of medicament and only uses an injection device with this single type of medicament. Furthermore, determination of the type of medicament may be ensured otherwise (e.g. by the key-recess pair shown in FIG. 4 that the supplementary device is only useable with one specific injection device, which may then only provide this single type of medicament).

In a step 502, a currently selected dose is determined, for instance by OCR of information shown on a dosage window of injection device as described above. This information is then displayed to a user of the injection device in a step 503.

In a step 504, it is checked if an ejection has taken place, for instance by sound recognition as described above. Therein, a prime shot may be differentiated from an actual injection (into a creature) either based on respectively different sounds produced by the injection device and/or based on the ejected dose (e.g. a small dose, for instance less than a pre-defined amount of units, e.g. 4 or 3 units, may be considered to belong to a prime shot, whereas larger doses are considered to belong to an actual injection).

If an ejection has taken place, the determined data, i.e. the selected dose and—if applicable—the type of medicament (e.g. insulin), is stored in the main memory 241, from where it may later be transmitted to another device, for instance a blood glucose monitoring system. If a differentiation has been made concerning the nature of the ejection, for instance if the ejection was performed as a prime shot or as an actual injection, this information may also be stored in the main memory 241, and possibly later transmitted. In the case of an injection having been performed, at step 505 the dose is displayed on the display 21. Also displayed is a time since the last injection which, immediately after injection, is 0 or 1 minute. The time since last dose may be displayed intermittently. For instance, it may be displayed alternately with the name or other identification of the medicament that was injected, e.g. Apidra or Lantus.

If ejection was not performed at step 504, steps 502 and 503 are repeated.

After display of the delivered dose and time data, the flowchart 500 terminates.

FIG. 5b shows in more detail exemplary method steps that are performed when the selected dose is determined based on the use of optical sensors only. For instance, these steps may be performed in step 502 of FIG. 5a.

In a step 901, a sub-image is captured by an optical sensor such as optical sensor 25 of supplementary device 2. The captured sub-image is for instance an image of at least a part of the dosage window 13 of injection device 1, in which a currently selected dose is displayed (e.g. by means of numbers and/or a scale printed on the sleeve 19 of injection device 1, which is visible through the dosage window 13). For instance, the captured sub-image may have a low resolution and/or only show a part of the part of sleeve 19 which is visible through dosage window 13. For instance, the captured sub-image either shows the numbers or the scale printed on the part of sleeve 19 of injection device 1 which is visible through dosage window 13. After capturing an image, it is, for instance, further processed as follows:

Division by a previously captured background image;
Binning of the image(s) to reduce the number of pixels for further evaluations;
Normalization of the image(s) to reduce intensity variations in the illumination;
Sheering of the image(s); and/or
Binarization of the image(s) by comparing to a fixed threshold.

Several or all of these steps may be omitted if applicable, for instance if a sufficiently large optical sensor (e.g. a sensor with sufficiently large pixels) is used.

In a step 902, it is determined whether or not there is a change in the captured sub-image. For instance, the currently captured sub-image may be compared to the previously captured sub-image(s) in order to determine whether or not there is a change. Therein, the comparison to previously captured sub-images may be limited to the sub-image of the previously captured sub-images that was captured immediately before the current sub-image was captured and/or to the sub-images of the previously captured sub-images that were captured within a specified period of time (e.g. 0.1 seconds) before the current sub-image was captured. The comparison may be based on image analysis techniques such as pattern recognition performed on the currently captured sub-image and on the previously captured sub-image. For instance, it may be analyzed whether the pattern of the scale and/or the numbers visible through the dosage window 13 and shown in the currently captured sub-image and in the previously captured sub-image is changed. For instance, it may be searched for patterns in the image that have a certain size and/or aspect ratio and these patterns may be compared with previously saved patterns. Steps 901 and 902 may correspond to a detection of a change in the captured image.

If it is determined in step 902 that there is a change in the sub-image, step 901 is repeated. Otherwise in a step 903, an image is captured by an optical sensor such as optical sensor 25 of supplementary device 2. The captured image is for instance an image of the dosage window 13 of injection device 1, in which a currently selected dose is displayed (e.g. by means of numbers and/or a scale printed on the sleeve 19 of injection device 1, which is visible through the dosage window 13). For instance, the captured image may have a resolution being higher than the resolution of the captured sub-image. The captured image at least shows the numbers printed on the sleeve 19 of injection device 1 which are visible through the dosage window 13.

In a step 904, optical character recognition (OCR) is performed on the image captured in step 903 in order to recognize the numbers printed on the sleeve 19 of injection device 1 and visible through the dosage window 13, because these numbers correspond to the (currently) selected dose. In accord to the recognized numbers, the selected dose is determined, for instance by setting a value representing the selected dose to the recognized numbers.

In a step 905, it is determined whether or not there is a change in the determined selected dose and, optionally, whether or not the determined selected dose does not equal zero. For instance, the currently determined selected dose may be compared to the previously determined selected dose(s) in order to determine whether or not there is a change. Therein, the comparison to previously determined selected dose(s) may be limited to the previously determined selected dose(s) that were determined within a specified period of time (e.g. 3 seconds) before the current selected dose was determined. If there is no change in the determined selected dose and, optionally, the determined selected dose does not equal zero, the currently determined selected dose is returned/forwarded for further processing (e.g. to processor 24).

Thus, the selected dose is determined if the last turn of the dosage knob 12 is more than 3 seconds ago. If the dosage knob 12 is turned within or after these 3 seconds and the new position remains unchanged for more than 3 seconds, this value is taken as the determined selected dose.

FIG. 5c shows in more detail method steps that are performed when the selected dose is determined based on the use of acoustical and optical sensors. For instance, these steps may be performed in step 502 of FIG. 5a.

In a step 1001, a sound is captured by an acoustical sensor such as acoustical sensor 27 of supplementary device 2.

In a step 1002, it is determined whether or not the captured sound is a click sound. The captured sound may for instance be a click sound that occurs when a dose is dialed by turning dosage knob 12 of injection device 1 and/or when a dose is ejected/injected by pressing injection button 11, and/or when a prime shot is performed. If the captured sound is not a click sound, step 1001 is repeated. Otherwise in a step 1003, an image is captured by an optical sensor such as optical sensor 25 of supplementary device 2. Step 1003 corresponds to step 903 of flowchart 900.

In a step 1004, an OCR is performed on the image captured in step 1003. Step 1004 corresponds to step 904 of flowchart 900.

In a step 1005, it is determined whether or not there is a change in the determined selected dose and, optionally, whether or not the determined selected dose does not equal zero. Step 1005 corresponds to step 905 of flowchart 900.

There might be a slight advantage of the acoustic approach shown in FIG. 5c when it comes to power consumption of the supplementary device, because permanently capturing images or sub-images as shown in FIG. 5b typically is more power consuming than listening to an acoustical sensor such as a microphone.

Figure 6:
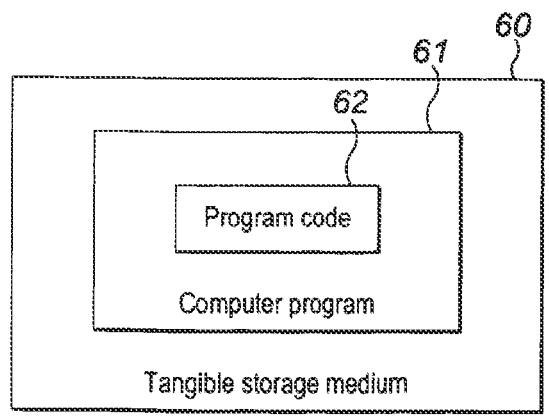
FIG. 6: a schematic illustration of a tangible storage medium 60 according to an embodiment of the present invention.

FIG. 6 is a schematic illustration of a tangible storage medium 60 (a computer program product) that comprises a computer program 61 with program code 62 according to aspects of the present invention. This program code may for instance be executed by processors contained in the supplementary device, for instance processor 24 of supplementary device 2 of FIGS. 2a and 4. For instance, storage medium 60 may represent program memory 240 of supplementary device 2 of FIG. 4. Storage medium 60 may be a fixed memory, or a removable memory, such as for instance a memory stick or card.

Figure 7:
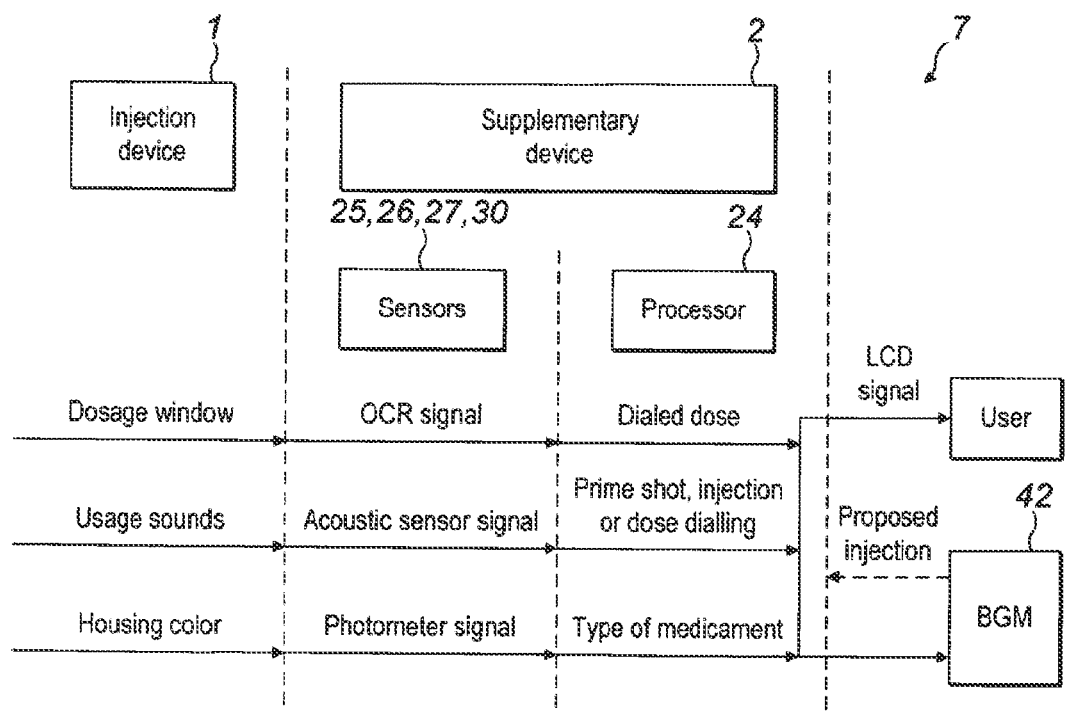
FIG. 7: an information sequence chart that illustrates an information flow between various devices according to embodiments of the invention.

Finally, FIG. 7 is an information sequence chart 7 that illustrates the flow of information between various devices (e.g. the injection device 1 and the supplementary device 2 of FIG. 4 in a scenario as depicted in FIG. 3a or 3b) according to an embodiment of the present invention. A condition and/or use of injection device 1 affects an appearance of its dosage window, sounds generated by injection device 1 and a colour of the housing. This information is transformed by sensors 25, 26, 27, 30 of supplementary device 2 into an OCR signal, an acoustic sensor signal and a photometer signal, respectively, which are in turn transformed into information on the dialed dose, on an injection/dialling operation and on the type of insulin by a processor 24 of supplementary device 2, respectively. This information is then provided by supplementary device 2 to a blood glucose monitoring system 42. Some or all of this information is displayed to a user via the display 21.

As described in detail above, embodiments of the present invention allow connection of a standard injection device, in particular an insulin device, with a blood glucose monitoring system in a useful and productive way.

Embodiments of the present invention introduce a supplementary device to allow for this connection, assuming the blood glucose monitoring system has wireless or other communication capabilities.

The benefits from the connection between the blood glucose monitoring and an insulin injection device are inter alia the reduction of mistakes by the user of the injection device and a reduction of handling steps—no more manual transfer of the injected insulin unit to a blood glucose monitoring is required, in particular to a blood glucose monitoring system with functionality of providing guidance for the next dose based on the last dose injected and latest blood glucose values.

As described with reference to exemplary embodiments above, when a user/patient gets a new insulin pen, the user attaches the supplementary device to the pen. The supplementary device reads out the injected dose. It may also transfer it to a blood glucose monitoring system with insulin titration capabilities. For patients taking multiple insulins, the supplementary device recognizes the device structure to the insulin type and may also transmit this piece of information to the blood glucose monitoring system.

In example embodiments, the information shown on a display, for example LCD display 21 of FIGS. 2a and 4, may also converted to a sound signal played to a user through a speaker, for example by a text-to-speech functionality implemented by processor 24 using the acoustical signal generator 23. Thus, a user with impaired vision may have improved access to the information of supplementary device 2, such as a dialed dose, a recommended dose, a recommended time for administration and/or the like.

When using embodiments of the present invention, the user inter alia has the following advantages:

The user can use the most convenient disposable insulin injector.

The supplementary device is attachable and detachable (reusable).

Injected dose information may be transferred to the blood glucose monitoring system automatically (no more transfer mistakes). Improved dose guidance may result from this as the blood glucose monitoring system calculates the dose to be taken.

Keeping of a manual data logbook may not be needed any more.

Furthermore, when deploying the supplementary device proposed by the present invention, patients may also be reminded of injecting their next dose by receiving an alarm signal, for instance, after an appropriate time after a first dose of a medicament (for instance insulin or heparin) has been injected.

Injected dose information may be transferred to any computerized system, for instance as input for any dose calculation or any other applicable therapeutic guidance calculation, or for the creation of an alarm signal, for instance to remind the user of taking the next dose.

The term "drug" or "medicament", as used herein, means a pharmaceutical formulation containing at least one pharmaceutically active compound, wherein in one embodiment the pharmaceutically active compound has a molecular weight up to 1500 Da and/or is a peptide, a proteine, a polysaccharide, a vaccine, a DNA, a RNA, an enzyme, an antibody or a fragment thereof, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exendin-3 or exendin-4 or an analogue or derivative of exendin-3 or exendin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des(B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-Y-glutamyl)-des(B30) human insulin; B29-N—(N-lithocholyl-Y-glutamyl)-des(B30) human insulin; B29-N-($\omega$-carboxyheptadecanoyl)-des(B30) human insulin and B29-N-($\omega$-carboxyheptadecanoyl) human insulin.

Exendin-4 for example means Exendin-4(1-39), a peptide of the sequence H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser-NH2.

Exendin-4 derivatives are for example selected from the following list of compounds:

H-(Lys)4-des Pro36, des Pro37 Exendin-4(1-39)-NH2,
H-(Lys)5-des Pro36, des Pro37 Exendin-4(1-39)-NH2,
des Pro36 Exendin-4(1-39),
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39); or
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39), wherein the group-Lys6-NH2 may be bound to the C-terminus of the Exendin-4 derivative;

or an Exendin-4 derivative of the sequence
des Pro36 Exendin-4(1-39)-Lys6-NH2 (AVE0010),
H-(Lys)6-des Pro36 [Asp28] Exendin-4(1-39)-Lys6-NH2,
des Asp28 Pro36, Pro37, Pro38Exendin-4(1-39)-NH2,
H-(Lys)6-des Pro36, Pro38 [Asp28] Exendin-4(1-39)-NH2,
H-Asn-(Glu)5des Pro36, Pro37, Pro38 [Asp28] Exendin-4(1-39)-NH2,
des Pro36, Pro37, Pro38 [Asp28] Exendin-4(1-39)-(Lys)6-NH2,
H-(Lys)6-des Pro36, Pro37, Pro38 [Asp28] Exendin-4(1-39)-(Lys)6-NH2,
H-Asn-(Glu)5-des Pro36, Pro37, Pro38 [Asp28] Exendin-4(1-39)-(Lys)6-NH2,
H-(Lys)6-des Pro36 [Trp(O2)25, Asp28] Exendin-4(1-39)-Lys6-NH2,
H-des Asp28 Pro36, Pro37, Pro38 [Trp(O2)25] Exendin-4(1-39)-NH2,
H-(Lys)6-des Pro36, Pro37, Pro38 [Trp(O2)25, Asp28] Exendin-4(1-39)-NH2,
H-Asn-(Glu)5-des Pro36, Pro37, Pro38 [Trp(O2)25, Asp28] Exendin-4(1-39)-NH2,
des Pro36, Pro37, Pro38 [Trp(O2)25, Asp28] Exendin-4(1-39)-(Lys)6-NH2,
H-(Lys)6-des Pro36, Pro37, Pro38 [Trp(O2)25, Asp28] Exendin-4(1-39)-(Lys)6-NH2, H-Asn-(Glu)5-des Pro36, Pro37, Pro38 [Trp(O2)25, Asp28] Exendin-4(1-39)-(Lys)6-NH2, H-(Lys)6-des Pro36 [Met(O)14, Asp28] Exendin-4(1-39)-Lys6-NH2, des Met(O)14 Asp28 Pro36, Pro37, Pro38 Exendin-4(1-39)-NH2, H-(Lys)6-des Pro36, Pro37, Pro38 [Met(O)14, Asp28] Exendin-4(1-39)-NH2, H-Asn-(Glu)5-des Pro36, Pro37, Pro38 [Met(O)14, Asp28] Exendin-4(1-39)-NH2, des Pro36, Pro37, Pro38 [Met(O)14, Asp28] Exendin-4(1-39)-(Lys)6-NH2, H-(Lys)6-des Pro36, Pro37, Pro38 [Met(O)14, Asp28] Exendin-4(1-39)-(Lys)6-NH2, H-Asn-(Glu)5 des Pro36, Pro37, Pro38 [Met(O)14, Asp28] Exendin-4(1-39)-(Lys)6-NH2, H-Lys6-des Pro36 [Met(O)14, Trp(O2)25, Asp28] Exendin-4(1-39)-Lys6-NH2, H-des Asp28 Pro36, Pro37, Pro38 [Met(O)14, Trp(O2)25] Exendin-4(1-39)-NH2, H-(Lys)6-des Pro36, Pro37, Pro38 [Met(O)14, Asp28] Exendin-4(1-39)-NH2, H-Asn-(Glu)5-des Pro36, Pro37, Pro38 [Met(O)14, Trp(O2) 25, Asp28] Exendin-4(1-39)-NH2, des Pro36, Pro37, Pro38 [Met(O)14, Trp(O2)25, Asp28] Exendin-4(1-39)-(Lys)6-NH2, H-(Lys)6-des Pro36, Pro37, Pro38 [Met(O)14, Trp(O2)25, Asp28] Exendin-4(S1-39)-(Lys)6-NH2, H-Asn-(Glu)5-des Pro36, Pro37, Pro38 [Met(O)14, Trp(O2) 25, Asp28] Exendin-4(1-39)-(Lys)6-NH2;

or a pharmaceutically acceptable salt or solvate of any one of the afore-mentioned Exendin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Antibodies are globular plasma proteins (~150 kDa) that are also known as immunoglobulins which share a basic structure. As they have sugar chains added to amino acid residues, they are glycoproteins. The basic functional unit of each antibody is an immunoglobulin (Ig) monomer (containing only one Ig unit); secreted antibodies can also be dimeric with two Ig units as with IgA, tetrameric with four Ig units like teleost fish IgM, or pentameric with five Ig units, like mammalian IgM.

The Ig monomer is a "Y"-shaped molecule that consists of four polypeptide chains; two identical heavy chains and two identical light chains connected by disulfide bonds between cysteine residues. Each heavy chain is about 440 amino acids long; each light chain is about 220 amino acids long. Heavy and light chains each contain intrachain disulfide bonds which stabilize their folding. Each chain is composed of structural domains called Ig domains. These domains contain about 70-110 amino acids and are classified into different categories (for example, variable or V, and constant or C) according to their size and function. They have a characteristic immunoglobulin fold in which two β sheets create a "sandwich" shape, held together by interactions between conserved cysteines and other charged amino acids.

There are five types of mammalian Ig heavy chain denoted by α, δ, ε, γ, and μ. The type of heavy chain present defines the isotype of antibody; these chains are found in IgA, IgD, IgE, IgG, and IgM antibodies, respectively.

Distinct heavy chains differ in size and composition; α and γ contain approximately 450 amino acids and δ approximately 500 amino acids, while μ and ε have approximately 550 amino acids. Each heavy chain has two regions, the constant region ($C_H$) and the variable region ($V_H$). In one species, the constant region is essentially identical in all antibodies of the same isotype, but differs in antibodies of different isotypes. Heavy chains γ, α and δ have a constant region composed of three tandem Ig domains, and a hinge region for added flexibility; heavy chains μ and ε have a constant region composed of four immunoglobulin domains. The variable region of the heavy chain differs in antibodies produced by different B cells, but is the same for all antibodies produced by a single B cell or B cell clone. The variable region of each heavy chain is approximately 110 amino acids long and is composed of a single Ig domain.

In mammals, there are two types of immunoglobulin light chain denoted by λ and κ. A light chain has two successive domains: one constant domain (CL) and one variable domain (VL). The approximate length of a light chain is 211 to 217 amino acids. Each antibody contains two light chains that are always identical; only one type of light chain, κ or λ, is present per antibody in mammals.

Although the general structure of all antibodies is very similar, the unique property of a given antibody is determined by the variable (V) regions, as detailed above. More specifically, variable loops, three each the light (VL) and three on the heavy (VH) chain, are responsible for binding to the antigen, i.e. for its antigen specificity. These loops are referred to as the Complementarity Determining Regions (CDRs). Because CDRs from both VH and VL domains contribute to the antigen-binding site, it is the combination of the heavy and the light chains, and not either alone, that determines the final antigen specificity.

An "antibody fragment" contains at least one antigen binding fragment as defined above, and exhibits essentially the same function and specificity as the complete antibody of which the fragment is derived from. Limited proteolytic digestion with papain cleaves the Ig prototype into three fragments. Two identical amino terminal fragments, each containing one entire L chain and about half an H chain, are the antigen binding fragments (Fab). The third fragment, similar in size but containing the carboxyl terminal half of both heavy chains with their interchain disulfide bond, is the crystallizable fragment (Fc). The Fc contains carbohydrates, complement-binding, and FcR-binding sites. Limited pepsin digestion yields a single F(ab')2 fragment containing both Fab pieces and the hinge region, including the H—H interchain disulfide bond. F(ab')2 is divalent for antigen binding. The disulfide bond of F(ab')2 may be cleaved in order to obtain Fab'. Moreover, the variable regions of the heavy and light chains can be fused together to form a single chain variable fragment (scFv).

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

Figure 8A:
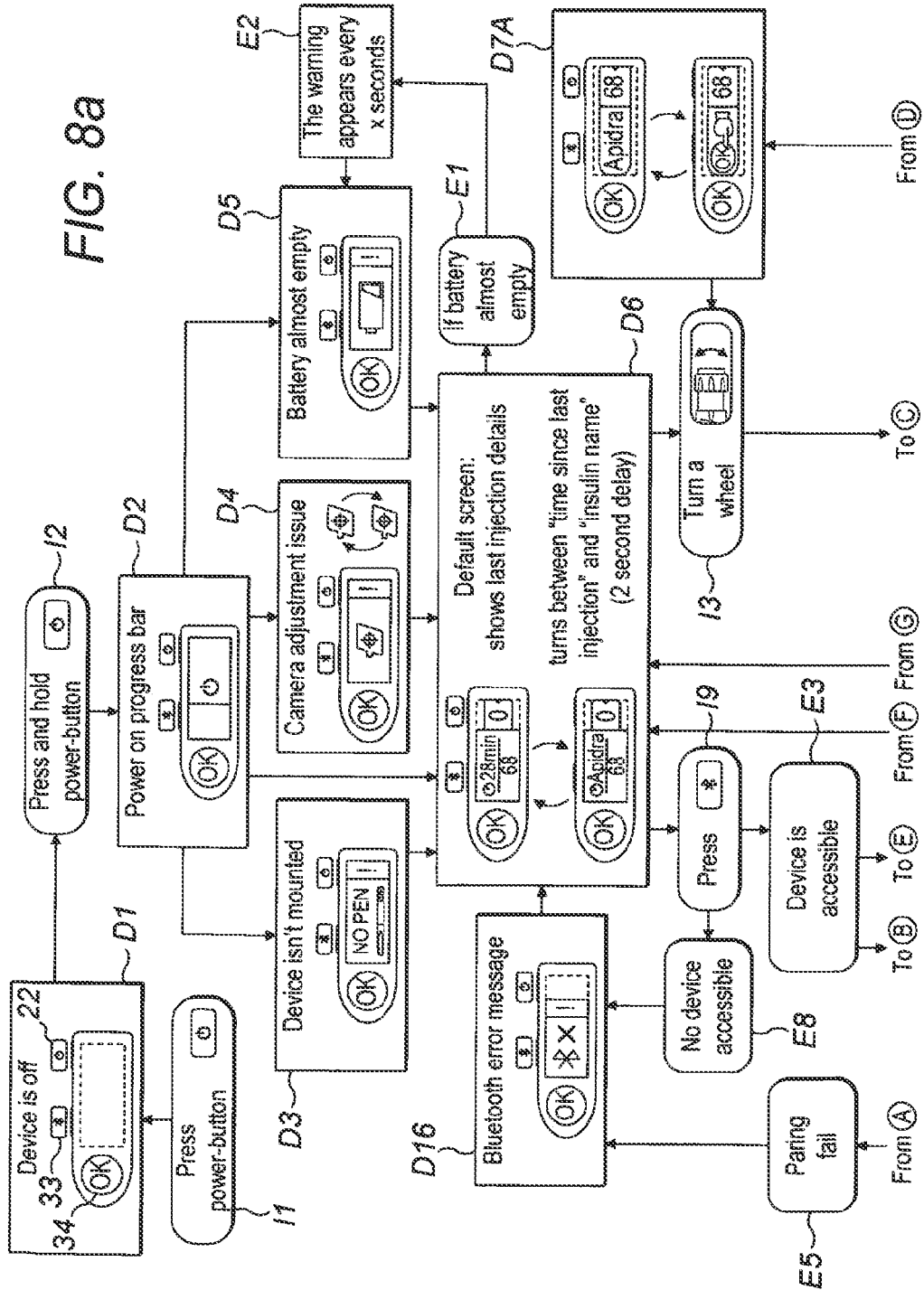
FIG. 8 (shown on two sheets FIG. 8a and FIG. 8b): a state diagram and flowchart illustrating operation of the device of FIG. 2b according to aspects of the invention.
Figure 8B:
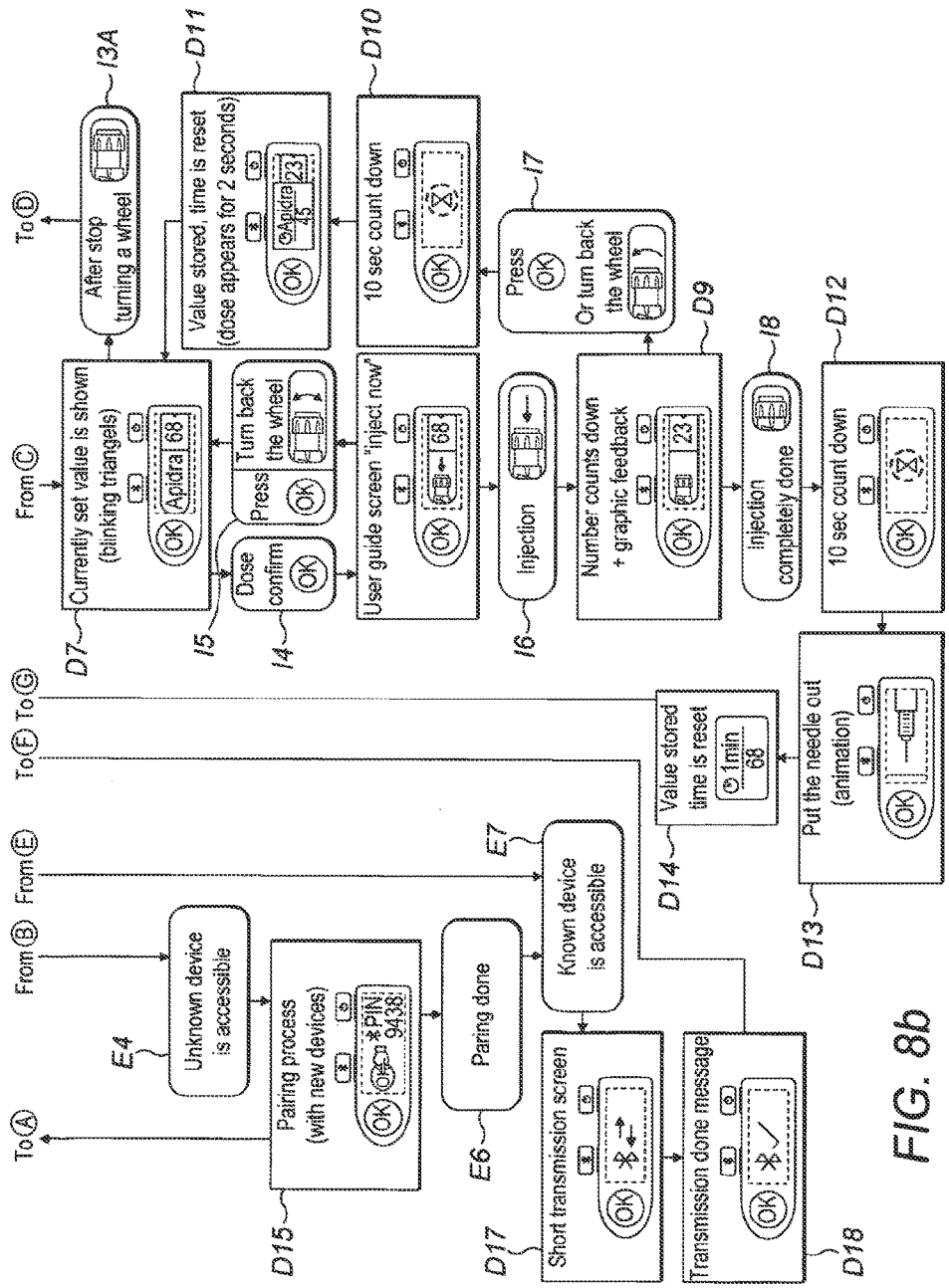

FIG. 8 is a drawing that will now be used to illustrate operation of the supplemental device 2. FIG. 8 is part flowchart and part state diagram.

In the following, user inputs are denoted with reference numerals commencing "I", displays or states are denoted with reference numerals commencing with "D", and other elements of the drawing, for instance checks made by the supplemental device and explanatory information, are denoted by reference numerals commencing with "E".

In the following, the display 21 is referred to as the LCD 21, so as to avoid confusion between the hardware display 21 and the image that is displayed, and which may be termed a display. However, the LCD 21 may be any suitable form of display hardware.

Initially, the supplemental device is powered off. This provides the display shown in D1.

D1 also goes to show the general arrangement of the user interface features of the supplemental device. In particular, an uppermost surface of the supplemental device 2 is shown provided with the LCD 21 and the confirm/OK button 34. The confirm/OK button 34 is located to the left of the LCD 21 in this example, although it may have an alternative location in other embodiments. The power on/off button 22 and the communications button 33 are located on the side of the supplemental device 2. As shown here, the communications button 34 and the power on/off button 22 are located on the same side of the supplemental device 2, although in other embodiments the buttons are located differently. For instance, in some embodiments, the power on/off button 22 is located on the opposite side of the LCD 21 to the communications button 33. In some other embodiments, the communications button 33 and/or the power on/off button 22 are located on the top surface of the supplemental device 2.

At input I1, the user presses the power on/off button 22. The input I1 is detected by the supplemental device 2. In particular, the processor 24 detects that the power on/off button 22 has been pressed for a relatively short period. Other user inputs are detected by the supplemental device in a similar manner, and short hand explanation is occasionally provided in the following explanation. In the following, 'mode' and 'state' are used interchangeably to denote the same thing; if the supplemental device 2 is in mode X it means the same as it being in state X.

If when the supplemental device 2 is in the state illustrated in D1, the supplemental device 2 receives a long press of the power on/off button 22, denoted at input I2 in FIG. 8, the supplemental device 2 transitions to the state or display shown at D2. Here, a power on progress bar is displayed on the LCD 21. This progress bar includes a symbol denoting power or a battery and also includes an indicator relating to the power level of the battery. As shown in FIG. 8, the battery power is approximately one third of the full battery in this example. The supplemental device 2 remains in the state indicated by D2 for a predetermined time, for instance 2 or 3 seconds. Following the state indicated in D2, the supplemental device 2 transitions to one of four possible states.

If the supplemental device is not mounted on the injection device 1, as is detected by the supplemental device by the processor 24 examining a state of the detection switch 30, the supplemental device 2 transitions to the state indicated by D3 in FIG. 8. Here, the supplemental device provides on the LCD 21 a graphic indicating that no pen is present. This may be purely graphical, purely textual, or a combination of graphics and text.

If when the supplemental device 2 is in the state indicated by D2, the supplemental device 2 detects that there is not correct alignment between the supplemental device 2 and the injection pen 1, the supplemental device progresses to the state indicated by D4 in FIG. 8. An incorrect alignment between the supplemental device 2 and the injection device 1 may be detected by the supplemental device by examination of the symbols received by the OCR module 25 and/or the photometer 26.

Thirdly, if the supplemental device when in the state indicated by D2 detects that the battery 32 is almost empty, the supplemental device transitions to a low battery state indicated by D5 in FIG. 8. Here, a battery warning graphic is provided. This may take any suitable form.

If the supplemental device 2 does not transition into any of the three states indicated by D3, D4 and D5 in FIG. 8, it transitions to the state indicated by D6. This is called the default state. In the default state, the supplemental device indicates details of the last injection. Put another way, in the default state, the supplemental device 2 displays information relating to the last use of the injection pen 1.

The default state D6 is also arrived at following the unmounted state indicated by D3, the incorrect alignment state indicated by D4 or the low battery state indicated by D5. The supplemental device 2 may remain in any of these preceding states for a predetermined time, for instance 3 seconds, 5 seconds or 10 seconds, before transitioning to the default state, shown in D6.

In the case of the unmounted state indicated by D3, the supplemental device 2 may instead refrain from transitioning to the default state indicated by D6 until the supplemental device 2 detects that there is correct alignment between the supplemental device 2 and the injection pen 1. Alternatively, after the supplemental device has transitioned through the unmounted state indicated by D3, the supplemental device may remain in the default state indicated by D6 until the supplemental device detects, by examining the state of the detection switch 30, that the supplemental device 2 is mounted on the injection device 1.

With respect to the unaligned state indicated by display D4 in FIG. 8, the supplemental device 2 may remain in the unaligned state until the supplemental device 2 detects correct alignment between the supplemental device 2 and the injection device 1. Alternatively, the supplemental device 2 may transition from the unaligned state indicated by D4 to the default state indicated by D6 but refrain from progressing from the default state until the supplemental device 2 detects that there is correct alignment between the supplemental device 2 and the injection device 1.

If the supplemental device has transitioned through the low battery state indicated by D5 before arriving at the default state indicated by D6 in FIG. 8, the supplemental device 2 indicates periodically that there is a low battery state. This is achieved by a check step E1 that depends from the default state D6. The check step E1 involves the supplemental device 2 determining whether the battery 32 is almost empty and, if so, an action step E2 involves providing the warning shown in the display D5 periodically.

Even if the supplemental device 2 did not transition through the low battery state indicated by D5 before arriving at the default state indicated by D6, the check step E1 is performed periodically. Thus, when the supplemental device 2 is in the default state, indicated by D6 in FIG. 8, and the battery level falls such that at the check step E1 it is determined that the battery is almost empty, action step E2 involves causing the supplemental device 2 to transition to the low battery state indicated by D5.

Once the low battery state D5 has been transitioned through, the low battery display indicated by D5 is provided periodically until the battery 32 is replaced or otherwise replenished. In some embodiments, the low battery display indicated in D5 is provided only when the supplemental device 2 is in the default state. This prevents the low battery warning being provided to the user when the device is in use in connection with delivery of a dose of medicament and/or when the supplemental device 2 is attempting to communicate with another device.

Although not shown in FIG. 8, if when the supplemental device 2 is in the default state, indicated by D6 in the Figure, the supplemental device 2 receives a long press of the power on/off button 22, the supplemental device powers down. Thereafter, the device is in the off state that is indicated by D1 in FIG. 8. The supplemental device 2 may be responsive to a long press of the power on/off button 22 to power down from any state.

The supplemental device 2 may transition from the default state indicated by D6 in response to detecting that the user has turned the dosage dial 12. This is indicated at I3 in the Figure. In response, the supplemental device 2 enters a dosage dialling state, which is indicated at D7 in FIG. 8. Here, the supplemental device 2 displays on the LCD 21 the dose medicament that is currently dialed into the injection pen 1. This is known by the supplemental device 2 by virtue of reading of the figures (for example the numbers printed on the sleeve 19) from the injection device by the OCR reader 25. In this state, the supplemental device 2 also displays an indication of the medicament that is present within the injection device 1. In the display D7, the medicament is indicated through the display of text that names the medicament, in this case "Apidra".

The currently set dose is indicated in the dosage dialling state in the display shown in D7 in any suitable way. The dose advantageously is indicated in the largest characters that can be accommodated by the LCD 21. In particular, the height of the letters may be equal to the height of the LCD 21, or at least have a height that is 80 or 90% or more of the height of the LCD 21. The supplemental device may provide the display D7 in such a way as to make it clear to the user that the dose value displayed on the LCD 21 relates to a dose that is currently dialed into the injection pen in any suitable way. For instance, graphical elements provided around the displayed dose value may blink or flash. Alternatively, the characters of the dose value themselves may blink or flash. Alternatively, the background may blink or flash.

When the supplemental device 2 detects that the dosage dial 12 has not been turned for a predetermined period, for instance 0.5 seconds or 1 second, this is detected at input I3a (although it is actually absence of an input) and the supplemental device 2 transitions to a dose dialed state, which is indicated by the dialed dose display D7a in FIG. 8. In the dose dialed state, the supplemental device 2 causes the LCD 21 to provide two different displays, with the device 2 transitioning from one display to the other display and back again on a periodic basis. In the dose dialed state indicated by D7a, both displays include the dialed dose, and this is provided in the same location. The dialed dose may be displayed in the same way in both of the displays. One display indicates the medicament that is present in the injection device 1. In this example, this is indicated by text that names the medicament, in this case "Apidra". The other display includes an indication that a dose of medicament may be delivered. In this example, this is provided by a graphic of a hand with a confirm/OK button.

If while in the dose dialed state illustrated by D7a the supplemental device 2 receives an input relating to further turning of the dosage dial 12, indicated by input I3 in FIG. 8, the supplemental device again proceeds to the dosage dialling state that is indicated by D7 in the Figure.

If the supplemental device 2 detects that the confirm/OK button 34 has been operated by a user when the device is either in the dosage dialling state indicated by D7 or in the dose dialed state indicated by D7a, this input I4 causes transition to an inject now state, which is indicated by D8 in FIG. 8. In the inject now state, a graphic is provided indicating to the user that injection is possible.

If the confirm/OK button 34 is not detected to have been pressed within a predetermined time period after turning of the dosage dial stops, a dose confirmation reminder may be displayed. This may take any suitable form. For instance, the supplemental device 2 may display the dialed dose and a graphic suggesting that the confirm/OK button is pressed, for instance in the form of an arrow pointing at a representation of the confirm/OK button.

At the inject now stage or state, represented by D8 in FIG. 8, the user has two options. They may change the dose. This is achieved by the user selecting the confirm/OK button 34 and then turning the dosage dialler 12. This is detected as an input I5 by the supplemental device. In detecting the input I5, the supplemental device 2 reverts to the dose dialed state indicated by D7 in FIG. 8.

Alternatively, the user can inject the medicament. This is detected by the supplemental device 2 as an input I6. Input I6 causes transition to a dosage delivery state, indicated as D9 in FIG. 8. Here, the dose remaining dialed into the injection device 1 is displayed on the LCD 21. As the dose is delivered, the dose remaining becomes smaller. As such, the remaining dose value counts down from the dialed in dose towards zero.

If the user does not deliver the entire dose, this is detected by the supplemental device at input I7 either by detecting depression of the confirm/OK button 34 or by detecting that the user has turned back the dosage dialler 12. The input I7 causes transition to a ten second countdown state, indicated at the display D10 in the Figure. After the ten seconds have lapsed, the supplemental device 2 transitions to a partial dose delivered state, indicated by a display D11 in FIG. 8. Here, the supplemental device 2 displays the dose delivered to the user through the injection pen 1. The dose delivered is equal to the dose that was dialed in, as detected by the supplemental device when in the dosage dialling state indicated by D7 or the dialed dose state indicated by D7a, minus the dose remaining when the input I7 was detected. In this state, the medicament that was delivered also is displayed. In this example, the delivered dose is indicated in characters that are smaller than the characters provided by either of the states indicated by D7 and D7a in FIG. 8. Arranged vertically with respect to the delivered dose is an indication of the medicament that was delivered. On transitioning to or from this state, a timer (not shown) within the supplemental device is reset. The timer allows the supplemental device 2 to calculate an elapsed time since a last dose was delivered.

Transition from the state indicated by display D11 is to the state indicated by D7 in FIG. 8.

Alternatively, the supplemental device 2 may exit the dose delivery state indicated by D9 by detecting an input I8 indicative of the injection having been completed. In this case, the supplemental device transitioned to a countdown state that is indicated by the display D12 in FIG. 8. Here, the LCD 21 is provided with an icon that is the same as the icon provided in the display of the countdown state indicated by D10 in the Figure.

After ten seconds have elapsed, the supplemental device 2 transitions to a remove needle instruction state, indicated at the display D13 in FIG. 8. Here, the supplemental device 2 provides a graphic that indicates to the user that the needle of the injection device 1 should be replaced. After a predetermined time, or upon detecting that the needle has been replaced if the acoustical sensor 27 is present, the supplemental device 2 transitions to a reset state that is indicated by the display D14 in FIG. 8. Here, the value of the delivered dose is stored in the supplemental device 2 and a timer (not shown) is started. The timer provides a value that is indicative of the time elapsed since the last dose. After the reset state, the supplemental device 2 transitions to the default state, indicated by D6 in FIG. 8.

It is a special situation if, from the state indicated at D7, the user delivers a dose without confirming the dose by the input I4. This special situation is detected by the supplemental device 2 detecting injection, as with I6, from state D7 without first detecting operation of the confirm/OK button 34. In this special situation, the supplemental device 2 displays an injected dose storage screen (not shown) when it is detected that the dose delivery button is fully pushed down. In this case, no dose completion indicator is provided and no animation (such as that of D12) is started. The injected dose storage screen may be provided only upon detection that the dose delivery button has been depressed for more than 10 seconds, during which time the user should have kept the needle in their skin to ensure that the dose is fully delivered.

The injected dose storage screen (not shown) may indicate the dose volume that the supplemental device has determined was delivered. The injected dose storage screen (not shown) may provide a graphic suggesting that the user confirms the displayed dose. For instance, the graphic may be an animation of the OK button flashing. The injected dose storage screen (not shown) may also indicate the name of the medicament and/or the time of injection.

When the dose volume is displayed in the injected dose storage screen (not shown), the supplemental device is responsive to detecting inputs on the keys 32, 33 to increment or decrement the displayed dose. This allows the user to change the dose that is stored in the supplemental device 2.

Upon detecting pressing of the confirm/OK button 34, the supplemental device 2 stores the dose and time of delivery.

If when the supplemental device 2 is in the default state, indicated by D6, it detects an input I9 indicating that the user has pressed the communication button 33, it transitions from the default state. Here, the supplemental device 2 determines whether a device is accessible. A device here is for instance the blood glucose measurement unit 42. If a determination at step S3 indicates that a device is accessible and it is determined in E4 that the device is unknown, the supplemental device 2 enters a pairing process state, which is indicated by D15 in the Figure. In this state, the supplemental device 2 initiates pairing with the detected device. In the case of the wireless unit 28 being a Bluetooth transceiver, this involves initiating pairing in accordance with the Bluetooth standard. In the pairing process state, indicated by D15, a Bluetooth PIN number is displayed on the LCD 21. This is accompanied with an icon requesting that the user confirm that the PIN number matches with one displayed on the unknown device. If the supplemental device 2 determines at E5 that pairing has failed, the supplemental device 2 transitions to a Bluetooth error message state, indicated by D16 in the Figure. This state is also transitioned to following input I9 if it is determined at E8 that no device is accessible. In the Bluetooth error message state, indicated by D16, an icon is displayed on LCD 21 indicating that no communication is possible. Following the Bluetooth error message state, for instance after a predetermined time, the supplemental device 2 transitions to the default state, indicated by D6.

If in the pairing state the supplemental device at E6 determines that pairing has been completed, it transitions to a short transmission state, indicated by D17. The supplemental device also transmissions to the short transmission state indicated by D17 from the default state indicated by D6 following input I9 if the supplemental device determines that a device is accessible at E3 and at E7 determines that it is a known device.

In the short transmission state, indicated by D17, an icon or graphic is displayed on the LCD 21 indicating that communication is in process. Once communication is complete, the supplemental device 2 transitions to a transmission done stage, indicated by D18. Here, the supplemental device 2 provides a graphic indicating that transmission has been completed. Following the transmission done state, the supplemental device 2 transitions to the default state, indicated by D6.

When in the default state, indicated by D6, operation is as follows. The supplemental device 2 is expected to be in the default state for most of the time for which it is powered on. As such, the displays D6 when in the default state are the displays that are likely to be seen most by a user of the supplemental device.

When in the default state, the supplemental device is configured to indicate to the user details of the last delivered dose. The details include the quantity of the dose and the time elapsed since the last dose delivery. These details also include the identity of the medicament.

In these embodiments, this is achieved by transitioning between two different displays in the default state. The first display is shown uppermost in display D6 in FIG. 8. Here, it will be seen that there are two regions of the LCD 21. A region on the left side occupies approximately two thirds of the area of the display. This region is hereafter termed the last dose region. On the right side of the LCD 21, to the right of the last dose region, is another region. The other region in this example displays a dose that is dialed into the injection pen 1. The information displayed on the right side of the LCD 21 is the dialed value from the injection pen 1. This is not influenced by the information displayed on the left side of the LCD 21.

The last dose region in the first display, shown uppermost in D6 in FIG. 8, is divided into two areas. Here, they are upper and lower areas. In a first area, here the lower area, the last delivered dose is displayed. This is in the form of a number, indicating the dose in IUs.

In the second area, the elapsed time since the last dose delivered is displayed. Here, this is displayed as a time expressed as a number and with a unit of time expressed in Roman characters. Display of the unit of time allows a user to distinguish between the display of the time since the last dose and the quantity of the dose. The second area also includes a graphic indicating a timer or clock, which reinforces this message.

In the second display, shown lowermost in D6 in FIG. 8, the first area is unchanged. The first area thus displays the quantity of the last dose. The second area does not show the time elapsed since the last dose. Instead, it shows the medicament of the last dose. Here, this is indicated by text that spells the name of the medicament, in this case "Apidra". The clock or timer icon is again displayed in the second area.

In the default state, the supplemental device 2 causes the display to transition between the first and second displays, shown uppermost and lowermost respectively, periodically. Transitioning may occur every two seconds, for instance.

As can be seen in FIG. 8, the first area of the dose display region 21B is larger than the second area. As such, the height of the characters used to indicate the quantity of the dose are larger than the characters used to indicate the time elapsed since the last dose or the identity of the medicament. As such, a user is able to determine quickly and easily, perhaps with only a glance, the quantity of the last dose.

Additionally, the user is able to determine relatively easily the time elapsed since the last dose. It is the time elapsed since the last dose and the quantity of the dose that are the parameters that are most of interest to users of medicaments that are used to treat diabetes. It is these parameters that are most of interest to the user when determining the next dose of medicament, in terms of the time when it should be delivered and in terms of the quantity of medicament that may be needed.

As such, the provision of the default state and the displays provided in that state by the supplemental device 2 can allow the user better to treat the condition for which the medicament is prescribed. Put another way, the features of the supplemental device when in the default state can allow the user more easily to treat their condition, potentially providing better treatment for the user.

An alternative embodiment will now be described with reference to FIGS. 2c and 9.

As can be seen in FIG. 2c, the supplemental device 2 is provided with a LCD 21 and a power on/off button 22. The LCD 21 is a touch-sensitive display, through which a user can provide input to the supplemental device. As such, the touch-sensitive LCD 21 also provides the functions provided by the communications button 33 and the confirm/OK button 34 in the embodiment of FIG. 8 and FIG. 2b.

Operation of the supplemental device according to this embodiment is quite similar to the operation of the device of FIG. 2b, as described with reference to FIG. 8. In FIG. 9, reference numerals are retained from FIG. 8 for like elements, and only the differences between operation of the embodiment of FIG. 2c and the embodiment of FIG. 2b will be described here. For features and operation of the device of FIG. 2c that are the same as features and operations of the device of FIG. 2b and FIG. 8, no discussion is made in the following.

Figure 9B:
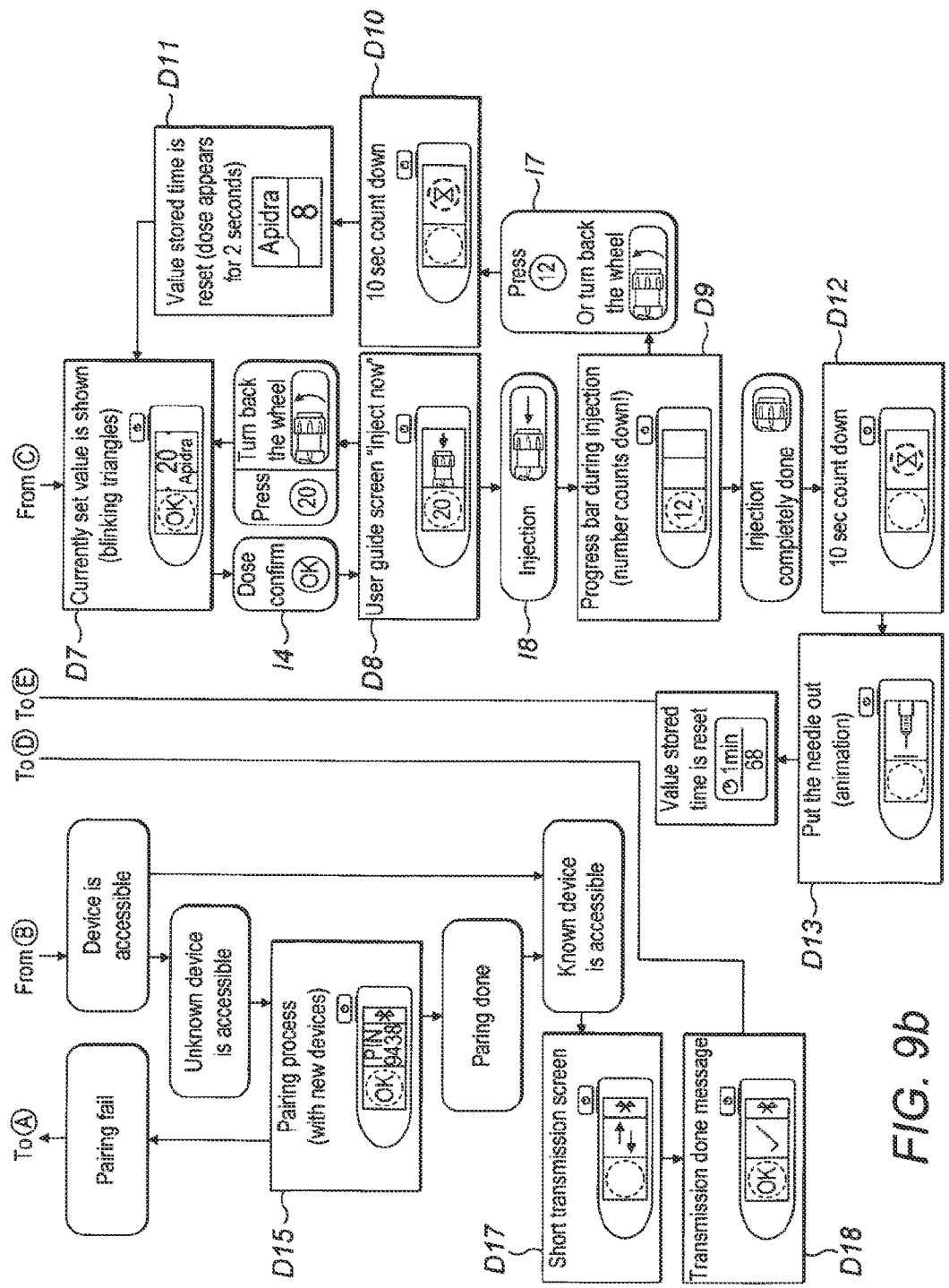
FIG. 9 (shown on two sheets FIG. 9a and FIG. 9b): a state diagram and flowchart illustrating operation of the device of FIG. 2c according to aspects of the invention.

The device off state, illustrated by display D1 in FIG. 9 is very similar to the corresponding state of the device operation shown in FIG. 8. This display D1 illustrates the overall layout provided on the LCD 21. In particular, a first region 21B of the display is a display region 21B. This is shown on the right of the display of D1 of FIG. 9. A second region 21A of the display is an input region 21A. This is shown on the left in D1. The input region 21A is also an active display region 21B. However, the input region 21A is a region where user inputs may be received. The input region 21A includes a display of a virtual button at appropriate times, in particular when the supplemental device 2 is in certain states. The input region 21A in this embodiment is always located in the same place on the LCD 21. This simplifies the experience for the user. In other embodiments, the input region 21A may change in location depending on the state of the supplemental device. The input region 21A is the touch sensitive input 35 shown in FIG. 2c.

In the device off state shown in D1, the LCD 21 is blank. When the LCD 21 is blank in a region, nothing is displayed in that region. When the input region 21A is blank, an outline of the virtual button may be displayed, although nothing is displayed within the virtual button.

In the power off progress state shown by D2, the input region 21A is left blank, that is nothing is displayed in the input region 21A. In this state, the display region 21B is provided with an indicator that indicates the amount of power remaining in the battery 32. This indicator is the same as the indicator shown in D2 of FIG. 8, although it is smaller in size.

In the device not mounted state D3, the input region 21A is blank, and a graphic indicating that the pen is not connected is shown in the display region 21B. In the camera adjustment issue state shown at D4, the input region 21A is left blank and the display region 21B indicates that there is not alignment between the supplemental device 2 and the injection device 1. In the battery low state indicated by display D5, the input region 21A is left blank and the display region 21B includes an icon indicating that the battery is almost empty.

In the default state, the input region 21A is provided with an icon relating to communication options. In this example, the input region 21A is provided with an icon indicating a Bluetooth communication option. The supplemental device 2 is configured when in the default state to respond to a user input I9 comprising touching of the LCD 21 at the input region 21A to proceed through the checks E3 and E8, as described above with reference to FIG. 8.

When in the default mode, the display region 21B of the display is provided with the displays as described above in relation to the first region of the display in the default state of FIG. 8.

If the supplemental device 2 detects that the battery is almost empty when the device is in the default state shown by D6, the check E1 may cause an action E2 which results in transitioning of the device to the battery almost empty state, providing a display shown in D5, periodically. Alternatively, the supplemental device 2 may be configured to include a low battery icon within the display region 21B. This is indicated by the display D19 in FIG. 9.

When in the currently set value state indicated by the display D7 in FIG. 9, the currently dialed dose is displayed in the display region 21B. The input region 21A is provided with a graphic, which in this case is the word "OK". When in this mode, the supplemental device 2 is responsive to detection of a user input at the input region 21A of the LCD 21, represented by input I4 in FIG. 9, to transition to the inject now state, illustrated by display D8 in FIG. 9. In the inject now state, the input region 21A is provided with an indication of the dialed dose. The display region 21B is provided with an icon which is the same as the icon shown in D8 of FIG. 8. After an injection input I8, the number displayed within the input region 21A counts down, reflecting the remaining dialed dose.

The supplemental device 2 is responsive to detection of a user input at the input region 21A of the LCD 21, indicated by input I7 in FIG. 9, to transition to the countdown state indicated by D10 in the Figure.

In the display indicated by display D11 in FIG. 9, the delivered dose is displayed, along with an indication of the medicament delivered.

In the countdown states indicated by the displays D10 and D12 in FIG. 9, the input region 21A of the LCD 21 is left blank. This is the case also for the remove needle state instruction provided by D13 in FIG. 9. In these states, no transition occurs from user input, so it is appropriate for the input region 21A of the LCD 21 to remain blank.

The communication error message state, indicated by D16, is similar to the corresponding display of FIG. 8. However, the input region 21A of the LCD 21 includes the text "OK". The supplemental device 2 is configured to transition from the communication error message state shown by D16 to the default state shown by D6 after a predetermined time or upon detecting a user input at the input region 21A of the LCD 21.

The text "OK" is provided at the input region 21A of the LCD 21 also when in the pairing state, indicated by display D15 in FIG. 9. The supplemental device 2 is configured to respond to detection of a user input at the input region 21A of the LCD 21 to transition either to the communication error message state shown by D16 or the short transmission state indicated by D17 depending on whether pairing has been achieved. Alternatively, transitioning may occur automatically, for instance in response to detection of a time out.

It will be appreciated from the above description of FIG. 9 that operation of the supplemental device of FIG. 2c is quite similar to the operation of the device of FIG. 2b. However, the dynamic adjustment of the text or graphics control to be displayed in the input region 21A of the LCD 21 simplifies the process of use for the user. In particular, aside from the power on/off button 22, there is only ever one input button/region 21A that needs to be operated by the user. Moreover, the consequence of the user operating the input should be more obvious.

Additionally, the arrangement of the supplemental device 2 of FIG. 2c is such that the user cannot operate the communications button other than when the device is in the default state, indicated by D6. This prevents the user believing that the supplemental device 2 might lead to actuation of the communications button 33 other than when in the default state, shown by D6.

It will be appreciated that the above-described embodiments are merely examples and that numerous alternatives will be envisaged by the skilled person and are within the scope of the present invention.

For instance, the communication states etc may be replaced by alternative states in which operation of the supplemental device 2 is quite different, or these states may be omitted altogether.

The invention claimed is:

1. A supplemental device for attachment to an injection device, the supplemental device comprising:
   a display;
   a processor arrangement comprising at least one sensor configured to detect a dose of medicament dialed into an attached injection device, determine that a dose of medicament has been delivered, and determine a quantity of medicament that has been delivered;
   at least one device, comprising a photometer, configured to:
      detect an optical property of a housing of the attached injection device or an optical property of a portion of a medicament container within the attached injection device viewable through a dosage window in the housing of the attached injection device; and
      determine an identity of a medicament present in the attached injection device based on the detected optical property of the housing or the detected optical property of the medicament container; and
   a clock configured to determine a current time;
   the processor arrangement being configured to continually display a quantity of medicament that was delivered as a last dose, and to alternate between displaying a time elapsed since delivery of the last dose and an identity of a medicament delivered in the last dose when the supplemental device is in a default mode, and
   wherein the processor arrangement is configured to respond to a delivery of less than an entire dose by transitioning the supplemental device to a partial dose delivered state, and to cause display of a dose delivered, wherein the dose delivered is equal to the dose of medicament dialed into the attached injection device minus an amount of dose remaining that was not delivered,
   wherein the display is a touch-sensitive display and wherein the processor arrangement is configured to cause display of a virtual button on the touch-sensitive display, the display indicating an action that the processor arrangement is configured to implement in response to receiving a user input at the virtual button, and
   wherein the processor arrangement is configured to respond to detection of a confirm/OK input by a user via the virtual button to cause display of a remaining dose dialed into the attached injection device, wherein the displayed remaining dose counts down as a dose is delivered.

2. A supplemental device as claimed claim 1, wherein the processor arrangement is configured to respond to detection of a dose being dialed, to enter the supplemental device into a dose dialing mode, and to cause display of a dose currently dialed into the attached injection device when the supplemental device is in the default mode.

3. A supplemental device as claimed in claim 2, wherein the processor arrangement is configured to respond to detection of dose dialing having stopped, to enter the supplemental device into a dose dialed mode, to cause display of a dose currently dialed into the attached injection device, and to display a graphic or text indicating that dose delivery is possible when the supplemental device is in the dose dialed mode.

4. A supplemental device as claimed in claim 1, wherein the processor arrangement is configured to respond to detection by at least one sensor of a dose having been delivered to enter the supplemental device into a dose delivered mode.

5. A supplemental device as claimed in claim 4, wherein the processor arrangement is configured to detect that a dose has been delivered by at least one sensor detecting that a dose has been fully delivered or by at least one sensor detecting that dose delivery has ceased and been confirmed by a user.

6. A supplemental device as claimed in claim 4, wherein the processor arrangement is configured to cause display of a delivered dose when the supplemental device is in the dose delivered mode.

7. A supplemental device as claimed in claim 4, wherein the processor arrangement is configured to respond to the supplemental device being detected to be in the dose delivered mode to record a time of dose delivery.

8. A system comprising a supplemental device as claimed in claim 1 and an injection device.

9. A method of operating a supplemental device attached to an injection device, the supplemental device being as claimed in claim 1, the method comprising:
- detecting a dose of medicament dialed into the injection device;
- determining that a dose of medicament has been delivered;
- determining a quantity of medicament that has been delivered; and
- when the supplemental device is in a default mode, displaying continually a quantity of medicament that was delivered as a last dose, and alternating between displaying a time elapsed since delivery of the last dose and an identity of the medicament delivered in the last dose.

10. A supplemental device for attachment to an injection device, the supplemental device comprising:
- a display;
- a processor arrangement comprising at least one sensor configured to detect a dose of medicament dialed into an attached injection device, determine that a dose of medicament has been delivered, and determine a quantity of medicament that has been delivered;
- a medicament determiner for determining an identity of a medicament present in the attached injection device, wherein the medicament determiner is configured to detect a code relating to the identity of a medicament present in the attached injection device; and
- a clock configured to determine a current time;
- the processor arrangement being configured to continually display a quantity of medicament that was delivered as a last dose, and to alternate between displaying a time elapsed since delivery of the last dose and an identity of the medicament delivered in the last dose when the supplemental device is in a default mode, and
- wherein the processor arrangement is configured to respond to a delivery of less than an entire dose by transitioning the supplemental device to a partial dose delivered state, and to cause display of the dose delivered, wherein the dose delivered is equal to the dose of medicament dialed into the attached injection device minus an amount of dose remaining that was not delivered;
- wherein the display is a touch-sensitive display and wherein the processor arrangement is configured to cause display of a virtual button on the touch-sensitive display, the display indicating an action that the processor arrangement is configured to implement in response to receiving a user input at the virtual button, and
- wherein the processor arrangement is configured to respond to detection of a confirm/OK input by a user via the virtual button to cause display of a remaining dose dialed into the attached injection device, wherein the displayed remaining dose counts down as a dose is delivered.

11. A supplemental device as claimed in claim 10, wherein the processor arrangement is configured to respond to detection of a dose being dialed by at least one sensor, to enter the supplemental device into a dose dialing mode, and to cause display of a dose currently dialed into the attached injection device when the supplemental device is in the default mode.

12. A supplemental device as claimed in claim 11, wherein the processor arrangement is configured to respond to detection by at least one sensor of dose dialing having stopped, to enter the supplemental device into a dose dialed mode, to cause display of a dose currently dialed into the attached injection device, and to display a graphic or text indicating that dose delivery is possible when the supplemental device is in the dose dialed mode.

13. A supplemental device as claimed in claim 10, wherein the processor arrangement is configured to respond to detection by at least one sensor of a dose having been delivered to enter a dose delivered mode.

14. A supplemental device as claimed in claim 13, wherein the processor arrangement is configured to detect by at least one sensor that a dose has been delivered by detecting that a dose has been fully delivered or by detecting by at least one sensor that dose delivery has ceased and been confirmed by a user.

15. A supplemental device as claimed in claim 13, wherein the processor arrangement is configured to cause display of a delivered dose when the supplemental device is in the dose delivered mode.

16. A supplemental device as claimed in claim 13, wherein the processor arrangement is configured to respond to the supplemental device being detected by at least one sensor to be in the dose delivered mode to record a time of dose delivery.

* * * * *

UNITED STATES PATENT AND TRADEMARK OFFICE
CERTIFICATE OF CORRECTION

PATENT NO. : 10,195,351 B2
APPLICATION NO. : 14/373138
DATED : February 5, 2019
INVENTOR(S) : Alexander Allerdings et al.

Page 1 of 1

It is certified that error appears in the above-identified patent and that said Letters Patent is hereby corrected as shown below:

In the Claims

In Column 26, Line 36, Claim 2, after "claimed" insert -- in --

Signed and Sealed this
Sixth Day of October, 2020

Andrei Iancu
*Director of the United States Patent and Trademark Office*